(12) United States Patent
Antoszczyk et al.

(10) Patent No.: US 11,072,810 B2
(45) Date of Patent: Jul. 27, 2021

(54) APPARATUS AND METHODS TO RAPIDLY DETECT, SEPARATE, PURIFY, AND QUANTIFY VARIOUS VIRUSES FROM CELLS, CULTURED MEDIUM AND OTHER FLUIDS

(71) Applicant: Fluid-Screen, Inc., Beverly, MA (US)

(72) Inventors: Slawomir Antoszczyk, Somerville, MA (US); Monika Weber, Fredericksburg, VA (US); Robert Weber, Dorchester, MA (US)

(73) Assignee: Fluid-Screen, Inc., Beverly, MA (US)

( * ) Notice: Subject to any disclaimer, the term of this patent is extended or adjusted under 35 U.S.C. 154(b) by 0 days.

(21) Appl. No.: 17/096,487

(22) Filed: Nov. 12, 2020

(65) Prior Publication Data
US 2021/0139944 A1     May 13, 2021

Related U.S. Application Data

(60) Provisional application No. 62/934,846, filed on Nov. 13, 2019.

(51) Int. Cl.
*G01N 1/18* (2006.01)
*C12Q 1/24* (2006.01)
(Continued)

(52) U.S. Cl.
CPC .......... *C12Q 1/24* (2013.01); *B01L 3/502761* (2013.01); *C12Q 1/04* (2013.01);
(Continued)

(58) Field of Classification Search
CPC ... C12Q 1/24; C12Q 1/04; C12Q 1/06; G01N 1/18; G01N 35/00; G01N 15/06;
(Continued)

(56) References Cited

U.S. PATENT DOCUMENTS 4,970,154 A    11/1990   Chang
5,622,588 A     4/1997   Weber
(Continued)

OTHER PUBLICATIONS

Extended European Search Report for European Application No. 15874123.1 dated Aug. 27, 2018.
(Continued)

*Primary Examiner* — Brian J. Sines
(74) *Attorney, Agent, or Firm* — Wolf, Greenfield & Sacks, P.C.

(57) ABSTRACT

Systems and methods are provided herein for rapid detection, separation, purification, and quantification of viral particles in a sample. According to some embodiments, a microfluidic device is provided for receiving the sample which may contain viral particles. An electrode of the microfluidic device may be used to generate dielectrophoretic (DEP) and/or electroosmotic (EO) forces acting on the sample. The applied DEP and/or EO forces may immobilize components of the sample on the surface of the electrode, may aggregate viral particles of the sample in one region of the microfluidic device, and may separate other components of the sample from the viral particles. The techniques may be performed rapidly, for example, in eight hours or less, and may not affect infectivity of the viral particles. In some embodiments, the sample may be labeled to enhance a response of one or more of the sample components to the DEP and/or EO forces.

20 Claims, 28 Drawing Sheets

(51) Int. Cl.
  *C12Q 1/04* (2006.01)
  *G01N 35/00* (2006.01)
  *G01N 15/06* (2006.01)
  *B01L 3/02* (2006.01)
  *B01L 3/00* (2006.01)

(52) U.S. Cl.
  CPC .................. *B01L 2200/0647* (2013.01); *B01L 2400/0424* (2013.01)

(58) Field of Classification Search
  CPC .. G01N 33/00; G01N 33/48; B01L 3/502761; B01L 2200/0647; B01L 2400/0424; B01L 3/02
  See application file for complete search history.

(56) References Cited

U.S. PATENT DOCUMENTS

| | | |
|---|---|---|
| 5,814,200 A | 9/1998 | Pethig et al. |
| 6,071,394 A | 6/2000 | Cheng et al. |
| 6,264,815 B1 | 7/2001 | Pethig et al. |
| 6,280,590 B1 | 8/2001 | Cheng et al. |
| 6,576,459 B2 | 6/2003 | Miles et al. |
| 6,875,329 B2 | 4/2005 | Washizu et al. |
| 6,887,362 B2 | 5/2005 | Huang et al. |
| 6,989,086 B2 | 1/2006 | Cheng et al. |
| 7,081,192 B1 | 7/2006 | Wang et al. |
| 7,115,422 B1 | 10/2006 | Gilton |
| 7,153,648 B2 | 12/2006 | Jing et al. |
| 7,169,282 B2 | 1/2007 | Talary et al. |
| 7,198,702 B1 | 4/2007 | Washizu et al. |
| 7,384,791 B2 | 6/2008 | Tyvoll et al. |
| 7,390,387 B2 | 6/2008 | Childers et al. |
| 7,390,388 B2 | 6/2008 | Childers et al. |
| 7,470,533 B2 | 12/2008 | Xu et al. |
| 7,534,334 B1 | 5/2009 | Fiechtner et al. |
| 7,615,762 B2 | 11/2009 | Satyanarayana et al. |
| 7,658,829 B2 | 2/2010 | Kanagasabapathi et al. |
| 7,666,289 B2 | 2/2010 | Simmons et al. |
| 7,686,934 B2 | 3/2010 | Hodko et al. |
| 7,744,738 B1 | 6/2010 | Gagnon et al. |
| 8,029,657 B1 | 10/2011 | Wu |
| 9,120,105 B2 | 9/2015 | Weber et al. |
| 2002/0036142 A1 | 3/2002 | Gascoyne et al. |
| 2003/0022393 A1 | 1/2003 | Seul et al. |
| 2004/0011651 A1 | 1/2004 | Becker et al. |
| 2004/0077074 A1 | 4/2004 | Ackley et al. |
| 2004/0109793 A1 | 6/2004 | McNeely et al. |
| 2004/0226819 A1 | 11/2004 | Talary et al. |
| 2005/0112544 A1 | 5/2005 | Xu et al. |
| 2005/0158704 A1 | 7/2005 | Tyvoll et al. |
| 2006/0226012 A1 | 10/2006 | Kanagasabapathi et al. |
| 2007/0125650 A1 | 6/2007 | Scurati et al. |
| 2008/0105565 A1 | 5/2008 | Davalos et al. |
| 2008/0134792 A1 | 6/2008 | Lee et al. |
| 2008/0221806 A1 | 9/2008 | Bryant et al. |
| 2009/0020428 A1 | 1/2009 | Levitan et al. |
| 2009/0294291 A1 | 12/2009 | Voldman et al. |
| 2009/0304644 A1 | 12/2009 | Hedrick et al. |
| 2010/0219075 A1 | 9/2010 | Furusawa |
| 2010/0297608 A1 | 11/2010 | Stern et al. |
| 2011/0147917 A1 | 6/2011 | England et al. |
| 2013/0105317 A1 | 5/2013 | Weber et al. |
| 2013/0118904 A1* | 5/2013 | Dickerson ............... B03C 5/005 204/547 |
| 2013/0292247 A1 | 11/2013 | Peyrade et al. |
| 2014/0083855 A1 | 3/2014 | Cheng et al. |
| 2015/0107999 A1 | 4/2015 | Weber et al. |
| 2015/0283553 A1 | 10/2015 | Charlot et al. |
| 2015/0318161 A1 | 11/2015 | Brown et al. |
| 2018/0080020 A1 | 3/2018 | Link et al. |
| 2018/0106759 A1 | 4/2018 | de Oliveira Botelho et al. |
| 2020/0179947 A1 | 6/2020 | Weber |

OTHER PUBLICATIONS

International Search Report and Written Opinion for International Application No. PCT/US2017/027659 dated Feb. 12, 2018.
International Search Report and Written Opinion for International Application No. PCT/US2015/65229 dated Feb. 16, 2016.
International Preliminary Report on Patentability for International Application No. PCT/US2015/065229 dated Jul. 6, 2017.
International Preliminary Report on Patentability for International Application No. PCT/US2017/027659 dated Oct. 25, 2018.
Extended European Search Report for European Application No. 17783251.6 dated Oct. 24, 2019.
Beving et al., Dielectric Properties of Human Blood and Erythrocytes at Radio Frequencies (0.2-10 MHz); Dependence on Cell Volume Fraction and Medium Composition. Eur Biophys J. 1994;23:207-15.
Carstensen, Passive Electrical Properties of Microorganisms. Biophysical Journal. 1967;7:493-503.
Chang et al., A Continuous Size-Dependent Particle Separator Using a Negative Dielectrophoretic Virtual Pillar Array. Lab Chip. 2008;8:1930-6.
Cheng et al., An Integrated Dielectrophoretic Chip for Continuous Bioparticle Filtering, Focusing, Sorting, Trapping, and Detecting. Biomicrofluidics. 1, 021503. 2007. 15 pages.
Cho et al., Creating, Transporting, Cutting, and Merging Liquid Droplets by Electrowetting-Based Actuation for Digital Microfluidic Circuits. Journal of Microelectromechanical Systems. 2003;12(1):70-80.
Choi et al., 3-Dimensional Electrode Patterning Within a Microfluidic Channel Using Metal Ion Implantation. Lab Chip. 2010;10(6):783-8.
Cociancich et al., Insect Defensin, an Inducible Antibacterial Peptide, Forms Voltage-Dependent Channels in Micrococcus Luteus. The Journal of Biological Chemistry. 1993;268(26);19239-45.
Fritz, Anomalous Diffusion of Erythrocytes in the Presence of Polyvinylpyrrolidone. Biophys. J. Society. 1984;46:219-228.
Ho et al., Rapid heterogeneous liver-cell on-chip patterning via the enhanced field-induced dielectrophoresis trap. Lab on a Chip. 2006;6:724-734. doi: 10.1039/b602036d.
Huang et al., Differences in the AC Electrodynamics of Viable and Non-Viable Yeast Cells Determined Through Combined Dielectrophoresis and Electrorotation Studies. Phys. Med. Biol. 1992;37(7):1499-517.
Kuczenski et al., Dielectrophoretic Microfluidic Device for the Continuous Sorting of *Escherichia coli* From Blood Cells. Biomicrofluidics. 2011;5:032005. 16 pages.
Lee et al., Electrowetting and Electrowetting-On-Dielectric for Microscale Liquid Handling. Sensors and Actuators A. 95. 2002:259-68.
Markx et al., Dielectrophoretic Characterization and Separation of Micro-Organisms. Microbiology. 1994;140:585-91.
Pethig, Review Article-Dielectrophoresis: Status of the Theory, Technology, and Applications. Biomicrofluidics. 2010;4:022811. 36 pages.
Pohl, Separation of Living and Dead Cells by Dielectrophoresis. Science. 1968;152:647-9.
Pohl et al., The Continuous Positive and Negative Dielectrophoresis of Microorganisms. Forum Press, Inc. J. Biol. Phys. 1981;9:67-86.
Pollack et al., Electrowetting-Based Actuation of Droplets for Integrated Microfluidics. Lab Chip. 2002;2:96-101.
Pollack et al., Electrowetting-Based Actuation of Liquid Droplets for Microfluidic Applications. Appl. Phys. Lett. 2000;77(11):1725-6.
Printen et al., Membrane Changes in Lipopolysaccharide-Stimulated Murine B Lymphocytes Associated With Cell Activation. Biochimica et Biophysica Acta. 1993;1148:91-96.
Shah et al., Specific binding and magnetic concentration of CD8+ T-lymphocytes on electrowetting-on-dielectric platform. Biomicrofluidics. 2010;4:044106. 13 pages.
Sher, Dielectrophoresis in Lossy Dielectric Media. Nature. 1968;220:695-6.
Stern et al., Label-free biomarker detection from whole blood. Nature Nanotechnology. 2010;5:138-42.

(56) References Cited

OTHER PUBLICATIONS

Stern et al., Label-free Electronic Detection of the Antigen-Specific T-Cell Immune Response Nano Lett. 2008;8(10):3310-4.
Surowiect et al., Dielectric Properties of Human B and T Lymphocytes A1 Frequencies From 20 kHz to 100 MHz. Phys. Med. Biol. 1986;31(1):43-53.
Unni et al., Characterization and Separation of Cryptosporidium and Giardia Cells Using On-Chip Dielectrophoresis. Biomicrofluidics 6, 012805. 2012. 25 pages.
Urdaneta et al., Multiple frequency dielectrophoresis. Electrophoresis. 2007;28:3145-55.
Vacic et al., Multiplexed SOI BioFETs. Biosens. Bioelectron. 2011;28:239-42.
Vahey et al., High-Throughput Cell and Particle Characterization Using Isodielectric Separation. Anal. Chemistry. 2009;81(7):2446-55.
Voldman, Electrical Forces for Microscale Cell Manipulation. Annual Review of Biomedical Engineering. 2006;8:425-54.
Wu, Biased AC Electro-Osmosis for On-Chip Bioparticle Processing. IEEE Transactions on Nanotechnology. 2006;5(2):84-89.
Xie et al., A three-phased circular electrode array for electro-osmotic microfluidic pumping. Microsyst Technol. 2011;17:367-72.
Yang et al., Dielectric Properties of Human Leukocyte Subpopulations Determined by Electrorotation as a Cell Separation Criterion. Biophysical Journal. 1999;76:3307-14.
Yang et al., Differential Analysis of Human Leukocytes by Dielectrophoretic Field-Flow-Fractionation. Biophysical Journal. 2000;78:2680-89.
Invitation to Pay Additional Fees dated Feb. 17, 2021 in connection with International Application No. PCT/US2020/060147.
Green et al., Manipulation and trapping of sub-micron bioparticles using dielectrophoresis. Journal of Biochemical and Biophysical Methods. Sep. 25, 1997;35(2):89-102.
Kim et al., Multitarget dielectrophoresis activated cell sorter. Analytical Chemistry. Nov. 15, 2008;80(22):8656-61. [NIH Public Access Author Manuscript].
PCT/US2020/060147, dated Apr. 22, 2021, International Search Report and Written Opinion.
International Search Report and Written Opinion dated Apr. 22, 2021 in connection with International Application No. PCT/US2020/060147.

* cited by examiner

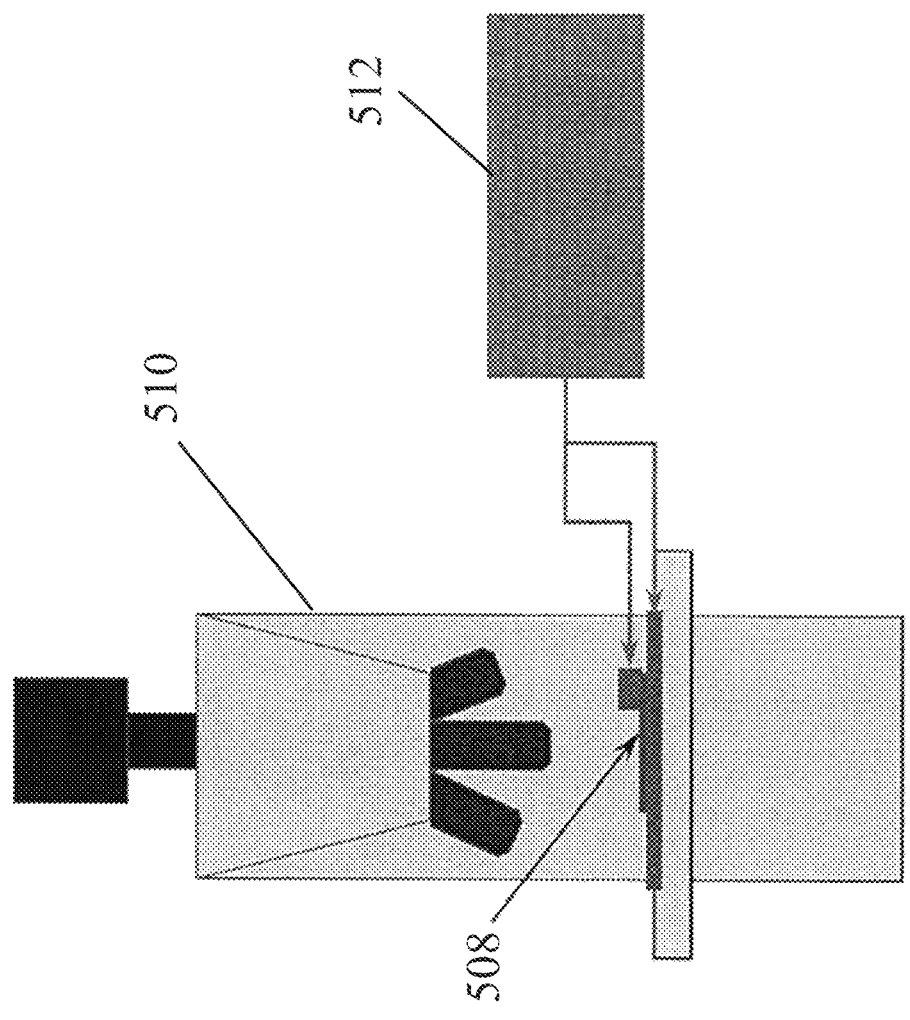

APPARATUS AND METHODS TO RAPIDLY DETECT, SEPARATE, PURIFY, AND QUANTIFY VARIOUS VIRUSES FROM CELLS, CULTURED MEDIUM AND OTHER FLUIDS

CROSS-REFERENCE TO RELATED APPLICATIONS

This application claims priority under 35 U.S.C. § 119(e) to U.S. Provisional Application Ser. No. 62/934,846, filed Nov. 13, 2019, titled "APPARATUS AND METHODS TO RAPIDLY SEPARATE, PURIFY, ENRICH, EXTRACT, DETECT, AND QUANTIFY VARIOUS VIRUSES FROM CELLS, CULTURED MEDIUM AND OTHER FLUIDS", which is incorporated by reference in its entirety herein.

BACKGROUND

Viruses are infectious agents of small size and simple composition that can replicate only in living cells of animals, plants, or bacteria. Viruses range in size from about 20 to 400 nanometers in diameter. A virus is the simplest form of organism, because unlike other organisms, the structure of a virus carries only its genetic material. Most viruses or virions (virus particles) consist of three main components: nucleic acid, a capsid and an envelope. Depending on the type of virus, viruses carry their genetic materials as RNA or DNA, and the function of the capsid or protein is to cover and protect the nucleic acid. The envelope structure is only present on certain viruses to protect the capsid. In some cases, a sample of a virus may contain impurities or capsids which are empty or partially filled and lack the DNA/RNA of the virus. Empty and partially filled capsids are therefore not able to be used in clinical applications which require fully packaged virus genomes, such as the use of viral vectors in gene therapy.

BRIEF SUMMARY

According to some embodiments, there is provided a method for separating viral particles (e.g., full capsids) from other components (e.g., empty and/or partially filled capsids) in a sample, the method comprising: directing the sample through at least one channel of a microfluidic device having at least one electrode arranged therein, the sample containing the viral particles; separating the viral particles from the other components of the sample by generating at least one dielectrophoretic force that acts on the sample using the at least one electrode; and detecting a presence of the viral particles in the sample based on a response of the viral particles to the at least one dielectrophoretic force generated by the at least one electrode.

In some embodiments, the method further comprises labeling the sample. In some embodiments, labeling the sample comprises labeling the sample with a chemical agent (e.g., gadolinium triacetate). In some embodiments, the chemical agent is configured to selectively label the viral particles or the other components in the sample. In some embodiments, selectively labeling the sample comprises labeling the other components with the chemical agent and not labeling the viral particles with the chemical agent. In some embodiments, the selectively labeling modifies a response of the other components to the at least one dielectrophoretic force acting on the sample. In some embodiments, the selectively labeling modifies a response of the viral particles to the at least one dielectrophoretic force acting on the sample.

In some embodiments, the method further comprises condensing the viral particles into a region subsequent to separating the viral particles from the other components of the sample. In some embodiments, the method further comprises flushing the other components from a region of the microfluidic device containing the at least one electrode.

In some embodiments, the method further comprises determining a quantity of the viral particles. In some embodiments, the method further comprises determining a quantity of the other components of the sample. In some embodiments, the method further comprises determining a ratio of the viral particles to the other components of the sample.

In some embodiments, the at least one electrode comprises at least one circular-shaped and/or partially-center-symmetric electrode. In some embodiments, an infectivity of the viral particles is unaffected by the directing, separating, and detecting. In some embodiments, each of the viral particles have a diameter of 400 nm or less.

According to some embodiments, there is provided a system configured to separate viral particles (e.g., full capsids) from other components (e.g., empty and/or partially filled capsids) in a sample, the system comprising: a microfluidic device comprising at least one channel having at least one electrode arranged therein, wherein the at least one channel is configured to receive the sample, the sample containing the viral particles; and a controller configured to: generate at least one dielectrophoretic force that acts on the sample using the at least one electrode to separate the viral particles from the other components; and detect a presence of the viral particles based on a response of the viral particles to the dielectrophoretic forces generated by the at least one electrode.

In some embodiments, the controller is further configured to label the sample. In some embodiments, labeling the sample comprises labeling the sample with a chemical agent (e.g., gadolinium triacetate). In some embodiments, the chemical agent is configured to selectively label the viral particles or the other components in the sample. In some embodiments, selectively labeling the sample comprises labeling the other components with the chemical agent and not labeling the viral particles with the chemical agent. In some embodiments, selectively labeling the sample modifies a response of the other components to the at least one dielectrophoretic force acting on the sample. In some embodiments, selectively labeling the sample modifies a response of the viral particles to the at least one dielectrophoretic force acting on the sample.

In some embodiments, the controller is further configured to condense the viral particles into a region subsequent to separating the viral particles form the other components of the sample. In some embodiments, the controller is further configured to flush the other components from a region of the microfluidic device containing the at least one electrode.

In some embodiments, the controller is further configured to determine a quantity of the viral particles. In some embodiments, the controller is further configured to determine a quantity of the other components. In some embodiments, the controller is further configured to determine a ratio of the viral particles to the other components of the sample.

In some embodiments, the at least one electrode comprises at least one circular-shaped and/or partially-center-symmetric electrode. In some embodiments, an infectivity of the viral particles is unaffected by the generating and detecting performed by the controller. In some embodiments, each of the viral particles have a diameter of 400 nm or less.

According to some embodiments, there is provided a method for separating components of a sample, the components comprising full capsid viral particles and empty and/or partially filled capsids, the method comprising: labeling the sample with a chemical agent (e.g., gadolinium triacetate), wherein the labeling modifies a response of the empty and/or partially filled capsids to at least one dielectrophoretic force acting on the sample relative to a response of the full capsid viral particles to the at least one dielectrophoretic force acting on the sample; directing the sample through at least one channel of a microfluidic device having at least one electrode arranged therein; generating, using the at least one electrode, the at least one dielectrophoretic force that acts on the sample, wherein the empty and/or partially filled capsids respond differently to the at least one dielectrophoretic force than the full capsid viral particles at least in part due to the labeling; and differentiating between the empty and/or partially filled capsids and the full capsid viral particles based on responses of the components of the sample to the at least one dielectrophoretic force.

In some embodiments, the labeling increases a difference between a dielectric function and/or a complex permittivity of each empty and/or partially filled capsid and a dielectric function and/or a complex permittivity of each full capsid viral particle. In some embodiments, the labeling increases a difference between a mass of each empty and/or partially filed capsid and a mass of each full capsid viral particle.

In some embodiments, the method further comprises determining a ratio of full capsid viral particles to empty and/or partially filled capsids. In some embodiments, the method further comprises separating the full capsid viral particles form the empty and/or partially filled capsids by condensing the full capsid viral particles into a region. In some embodiments, the method further comprises flushing the empty and/or partially filled capsids from a region of the microfluidic device containing the at least one electrode.

In some embodiments, the at least one electrode comprises at least one circular-shaped and/or partially-center-symmetric electrode. In some embodiments, an infectivity of the full capsid viral particles is unaffected by the labeling, directing, generating, and differentiating. In some embodiments, each of the full capsid viral particles and the empty and/or partially filled capsids have a diameter of 400 nm or less.

According to some aspects there is provided a system configured to separate components of a sample, the components comprising full capsid viral particles and empty and/or partially filled capsids, the system comprising: a microfluidic device comprising at least one channel having at least one electrode arranged therein, wherein the at least one channel is configured to receive the sample; and a controller configured to: direct the sample through the at least one channel of the microfluidic device, the sample being labeled with a chemical agent (e.g., gadolinium triacetate) that modifies a response of the empty and/or partially filled capsids to at least one dielectrophoretic force acting on the sample relative to a response of the full capsid viral particles to the at least one dielectrophoretic force acting on the sample; generate, using the at least one electrode, the at least one dielectrophoretic force that acts on the sample, wherein the empty and/or partially filled capsids respond differently to the at least one dielectrophoretic force than the full capsid viral particles at least in part due to the labeling; and differentiating between the empty and/or partially filled capsids and the full capsid viral particles based on responses of the components of the sample to the at least one dielectrophoretic force.

In some embodiments, the labeling increases a difference between a dielectric function and/or a complex permittivity of each empty and/or partially filled capsid and a dielectric function and/or a complex permittivity of each full capsid viral particle. In some embodiments, the labeling increases a difference between a mass of each empty and/or partially filed capsid and a mass of each full capsid viral particle.

In some embodiments, the controller is further configured to determine a ratio of full capsid viral particles to empty and/or partially filled capsids. In some embodiments, the controller is further configured to separate the full capsid viral particles form the empty and/or partially filled capsids by condensing the full capsid viral particles into a region. In some embodiments, the controller is further configured to flush the empty and/or partially filled capsids from a region of the microfluidic device containing the at least one electrode.

In some embodiments, the at least one electrode comprises at least one circular-shaped and/or partially-center-symmetric electrode. In some embodiments, an infectivity of the full capsid viral particles is unaffected by the labeling, directing, generating, and differentiating. In some embodiments, each of the full capsid viral particles and the empty and/or partially filled capsids have a diameter of 400 nm or less.

According to some embodiments there is provided a method for determining a ratio of full capsid viral particles to empty and/or partially filled capsids in a sample, the method comprising: labeling the sample with a chemical agent (e.g., gadolinium triacetate), the chemical agent selectively labeling only the empty and/or partially filled capsids of the sample; directing the sample through at least one channel of a microfluidic device having at least one electrode arranged therein; generating, using the at least one electrode, at least one dielectrophoretic force that acts on the sample, wherein the at least one dielectrophoretic force causes the empty and/or partially filled capsids and the full capsid viral particles to separate from each other at least in part due to the labeling; and subsequent to the generating the at least one dielectrophoretic force, determining a ratio of full capsid viral particles to empty and/or partially filled capsids.

In some embodiments, the labeling increases a difference between a dielectric function and/or a complex permittivity of each empty and/or partially filled capsid and a dielectric function and/or a complex permittivity of each full capsid viral particle. In some embodiments, the labeling increases a difference between a mass of each empty and/or partially filled capsid and a mass of each full capsid viral particle In some embodiments, each of the full capsid viral particles and the empty and/or partially filled capsids have a diameter of 400 nm or less. In some embodiments, the method further comprises flushing the empty and/or partially filled capsids from a region of the microfluidic device containing the at least one electrode.

BRIEF DESCRIPTION OF DRAWINGS

Various non-limiting embodiments of the technology will be described with reference to the following figures. It should be appreciated that the figures are not necessarily drawn to scale.

FIG. 5B illustrates an example manual system for rapidly detecting the presence of viral particles in a sample, according to some embodiments.

DETAILED DESCRIPTION

(1) Introduction

Aspects of the technology described herein relate to an apparatus and methods for enhancing efficiency of virus detection and purification from a fluid sample. In particular, the technology described herein provides techniques for rapid detection, separation, purification, and quantification of viral particles from a sample using a microfluidic system comprising electrodes for generating dielectrophoretic forces that act on the sample.

Figure 1B:
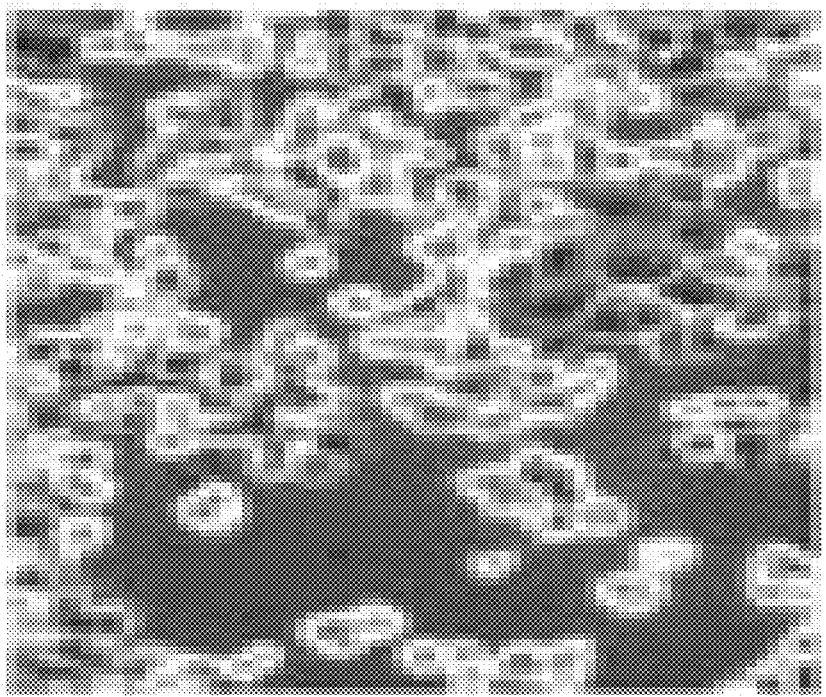
FIG. 1B is an example of cells infected with a virus which has caused morphological changes in the cells.
Figure 1A:
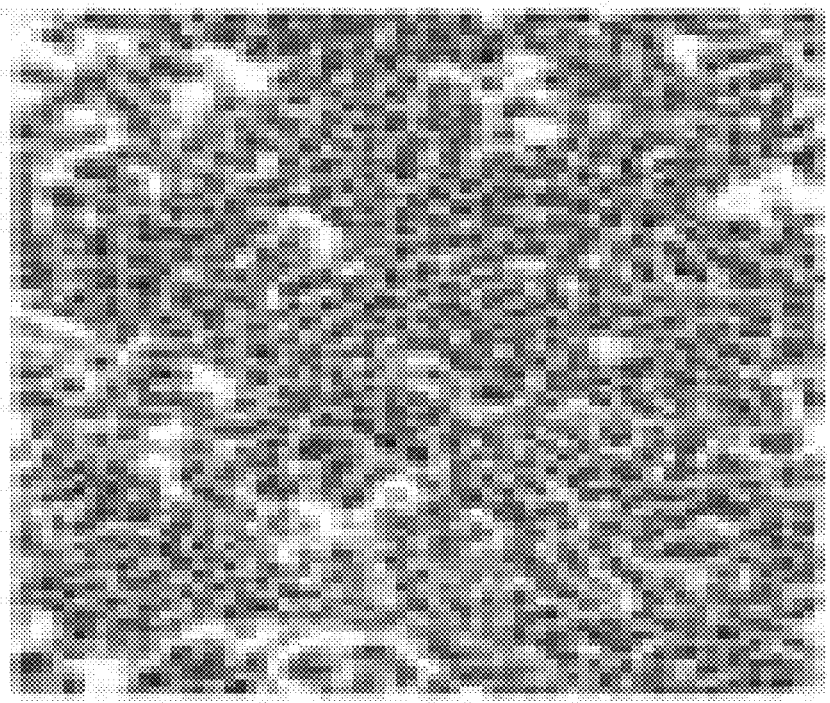
FIG. 1A is an example of uninfected cells.

Unlike bacterial, fungal, or mycoplasma contamination which can be relatively easily detected, viral contamination of a sample, such as a cell culture, may be difficult to detect, regardless of the scale of production, due to the small size of viral particles which range from 20 to 400 nm in diameter on average. Some viruses, for example, Herpes Simplex Virus (HSV), Epizootic Hemorrhagic Disease Virus (EHDV), and vesivirus 2117, can cause morphological changes to infected cells referred to as cytopathic effects (CPE). For example, FIG. 1A is an example of uninfected cells. FIG. 1B is an example of cells infected with a virus which has caused morphological changes in the cells. As shown in FIGS. 1A-1B, viral contamination is easily detected, for example, using microscopy, due to the CPE present in the infected cells. However, many viruses, such as Minute virus of mice (MVM), Bovine polyomavirus, and Reovirus, do not cause changes to the morphology of cells and thus contamination of a sample with these viruses remains difficult to detect.

Such kinds of viral contamination are dangerous for cell cultures, operators, and patients, for example, when a product developed using the sample (e.g., a vaccine, antibody for immunotherapy, gene therapy, and/or any other medicine) is administered to the patient. Viral contamination of samples may, in some cases, result in patient death. The difficulty of detecting viruses is therefore a serious problem in the biotechnological and pharmaceutical industries, amplified by the fact that there are currently no effective methods of decontaminating an affected sample. Thus, presently, the only practical way to keep samples virus-free is preventing viral contamination of samples (e.g., cells, animal derived compounds such as serums) at the outset. As such, the ability to accurately detect the presence of viral particles in a sample is of great significance.

The inventors have recognized, however, that conventional methods for virus detection have significant drawbacks. For example, conventional methods for virus detection often require infecting animals with a sample and waiting days or even weeks to observe an immune response. Some methods require detection of antibodies against viruses in order to detect the presence of a virus. Further still, some methods, such as genomic detection methods, require complex sample preparation. Thus, conventional methods for virus detection are expensive and time-consuming.

The inventors have recognized that techniques for virus detection may be improved upon through use of a microfluidic device (e.g., a chip) in combination with electrodes generating dielectrophoretic (DEP) forces and/or electroosmosis (EO). Using DEP and/or EO, it is possible to rapidly detect and quantify viruses, as well as purify and/or separate viral particles, in samples including biological fluids, water, cell culture media, etc. In some embodiments, the DEP and/or EO techniques may be combined with sample labelling (e.g., with fluorescent and/or small molecule stains which bind to primary amines on capsid proteins, for example) which may further enhance the response of viral particles to the DEP and/or EO forces. The techniques described herein may allow for rapid detection of viral contamination of a sample, even without the presence of morphological changes to the contaminated sample. For example, in some embodiments, detection of viral particles in a sample may be performed according to aspects of the techniques described herein in 8 hours or less. In some embodiments, detection of viral particles in a sample may be performed in 3 hours or less.

Aspects of the technology described herein further provide an apparatus and methods for purification and/or separation of viral particles from a fluid sample. Separation and/or purification of viral particles involves the separation of fully packaged cap sids containing DNA and/or RNA in the capsids from impurities in the viral sample containing only empty capsids and/or partially filled cap sids. Currently, conventional methods for separation and purification of viruses, such as adenovirus (Ad) or recombinant adeno-associated virus (rAAV), have many challenges, are extremely laborious, and may be prohibitively expensive. Examples of existing methods for purification of viruses in a fluid include: quantitative PCR (qPCR), immunoassay e.g. ELISA, high pressure liquid chromatography (HPLC), mass spectrometry (MS), electron microscopy (EM), analytical ultracentrifugation, affinity chromatography, cationic/anionic ion-exchange and size-exclusion chromatography (gel filtration). Despite the large number of purification/separation methods in the field, the conventional methods remain inadequate as results from these methods can take a large period of time to obtain (e.g., one or more days). Furthermore, results from virus purification/separation according to conventional methods are inconclusive and cannot guarantee 100% separation efficiency of empty capsids from full capsids, affecting the quality of the resulting product. In some cases, it is necessary to use a combination of two methods for virus purification/separation, which results in an even longer period of time for performing viral particle purification/separation, and consequently, an increase in cost. Therefore, there is a need for development of alternative methods for rapid purification/separation of viral particles in a fluid in order to use viruses such as rAAV in clinical practice, e.g. for use in gene therapy.

The inventors have recognized that the techniques described herein using a microfluidic device having electrodes for generating DEP forces and/or EO may be used to rapidly separate and/or purify a sample, for example, by separating full capsid viral particles from other components of the sample (e.g., empty and/or partially filled capsids). In some embodiments, the techniques described herein using DEP and/or EO may be used to determine a ratio of full capsid viral particles to empty and/or partially filled capsids. In some embodiments, the techniques described herein may be used to purify a sample, for example, by removing components other than the full capsid viral particles form the sample. Such techniques may, for example, be used in applications of gene therapy which use viral vectors to deliver DNA of a new gene into one or more cells. The inventors have appreciated that the separation, quantification, and purification techniques described herein may result in a more efficient process with higher separation efficiencies than conventional methods. In some embodiments, a system for performing rapid detection and/or purification of viruses in a fluid is an automated system for large-scale sorting of fully packaged viral genomes from impurities and empty capsids.

In some embodiments, the techniques described herein may be applied to assist in vaccine development. For example, the inventors have appreciated that conventional biological techniques require months or even years as well as billions of dollars to perform vaccine development, at least in part due to the high complexity of the vaccine development process. The inventors have recognized that vaccine development timelines, including virus purification and testing times, may be shortened through use of the techniques described herein for virus detection and/or separation.

The aspects and embodiments described above, as well as additional aspects and embodiments, are described further below. These aspects and/or embodiments may be used individually, all together, or in any combination, as the technology is not limited in this respect.

The term 'DEP' hereinafter refers to dielectrophoresis, or the force of an electric field gradient on objects having dielectric moments. The term 'O' refers to electroosmosis or the motion of liquid induced by an applied potential across a fluid conduit. The term 'CM factor' hereinafter refers to the Clausius-Mossotti factor upon which the DEP force depends.

(2) Example Techniques for Preparation of a Sample

Figure 2:
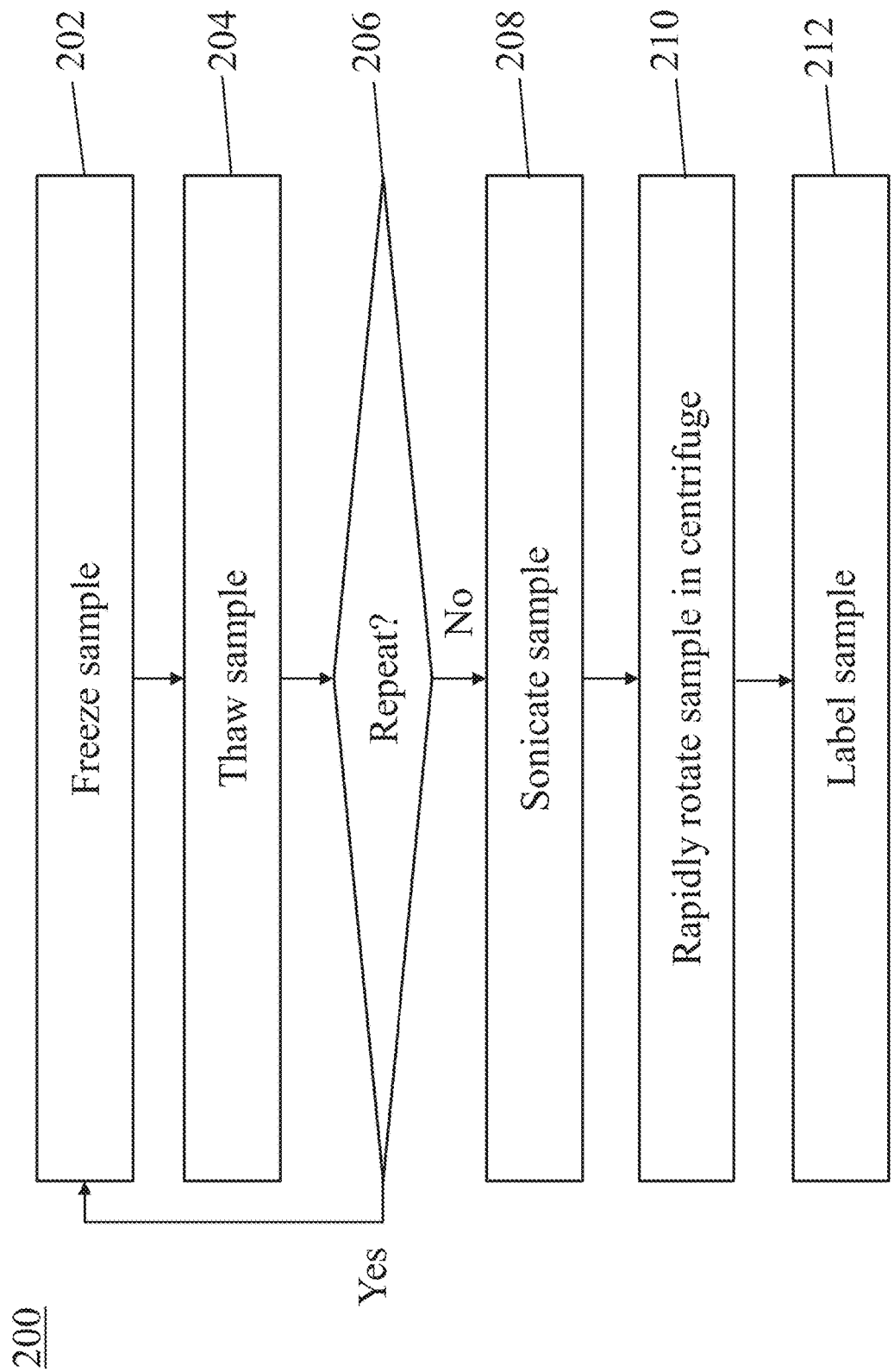
FIG. 2 illustrates an example process for preparing a fluid sample for processing in a microfluidic system, according to some embodiments.

Before performing the techniques described herein for detecting, separating, purifying and quantifying viruses in a fluid sample, techniques for preparing the sample may be performed. For example, FIG. 2 illustrates an example process for preparing a fluid sample for processing in a microfluidic system, according to some embodiments.

The sample may be a fluid solution containing viral particles and other components. Fluid samples may be regularly collected from a bioreactor at any phase of processing and such samples can then be prepared for processing in a microfluidic system according to the process 200, for example, such that the samples are compatible with the microfluidic system for effective processing. At act 202, a sample which may contain viral particles is frozen. In some embodiments, the sample may be frozen in a mixture comprising dry ice and ethanol (EtOH). Subsequently, at act 204, the sample is thawed.

At act 206 it may be determined whether to repeat acts 202-204 of freezing and thawing the sample. If, at act 206, it is determined that the process of freezing and thawing the sample is to be repeated, the process 200 may return through the yes branch to act 202. If, at act 206, it is determined that the process of freezing and thawing the sample need not be repeated, the process 200 may return through the no branch to act 208. The process of freezing and thawing the sample may be repeated any suitable number of times. For example, in some embodiments, the process of freezing and thawing the sample is repeated twice, such that the sample is frozen and thawed a total of three times before proceeding to act 208.

At act 208, the sample is sonicated. Sonicating the sample may separate cell debris from the supernatant sample containing viral particles. At act 210, the sample may be rapidly rotated in a centrifuge device. Rapidly rotating the sample may further clean the sample of any remaining cell debris. In some embodiments, one or more of acts 208-210 are repeated as desired to remove any remaining call debris from the sample before processing the sample in a microfluidic device.

At act 212, the sample may optionally be labeled. In some embodiments, labeling the sample comprises labeling the sample with a chemical agent, such as gadolinium triacetate, as is further described herein. In some embodiments, labeling the sample comprises staining the sample, for example, with a fluorescent dye. For example, DNA intercalators such as SyberGreen and/or Picogreen may be used to stain the sample prior to inputting the sample in the microfluidic system. In other embodiments, other stains such as Alexa-Flour 594 and 610x which bind to the primary amines of capsid proteins to create succinimidyl ester may be used. Any suitable labeling method and label may be used at act 212, and aspects the technology are not limited in this respect. Further, it should be appreciated that, in some embodiments, act 212 is omitted from process 200.

Figure 3B:
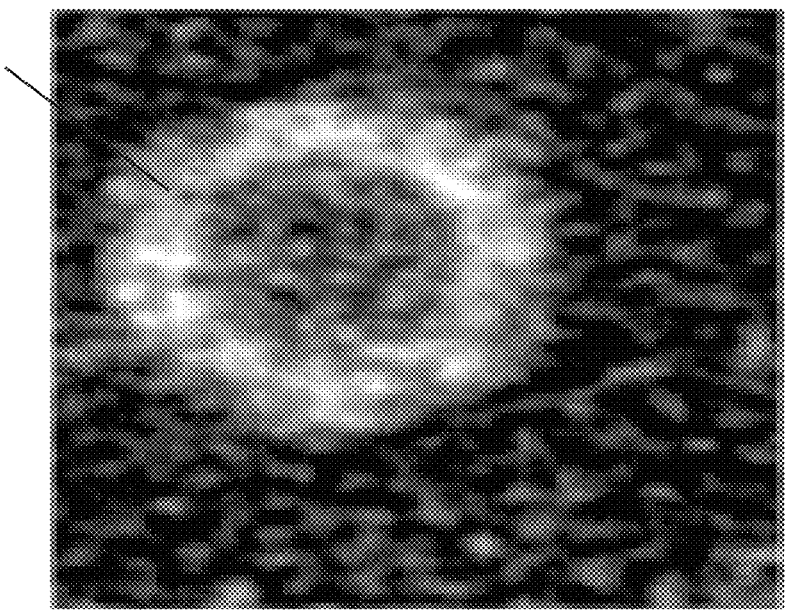
FIG. 3B shows an example of empty capsid exhibiting a ring-like architecture in response to labeling.
Figure 3A:
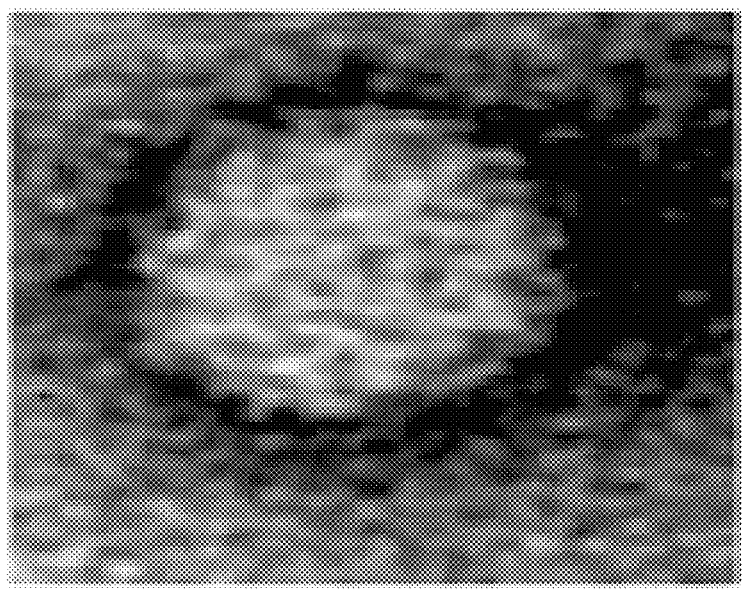
FIG. 3A shows an example of a fully packaged viral particle.

In some embodiments, the sample may be selectively labeled at act 212, for example, by labeling only some components of the sample and not others. For example, in some embodiments, selectively labeling the sample comprises labeling only other components of the sample and not labeling the viral particles. In some embodiments, selectively labeling the sample comprises labeling only viral particles and not other components of the sample. FIG. 3A shows an example of a fully packaged viral particle. In particular, the viral particle shown in FIG. 3A contains a full capsid which renders the viral particle impermeable to labeling with certain agents (e.g., uranyl acetate, gadolinium acetate). Thus, the viral particle shown in FIG. 3A is unaffected by labeling. By contrast, FIG. 3B shows an example of an empty capsid exhibiting a ring-like architecture 300 in response to labeling the sample.

In some embodiments, the sample is labeled using gadolinium triacetate, which is a non-radioactive heavy metal uranyl (radioisotope) acetate alternative. The inventors have recognized that the use of gadolinium triacetate is advantageous as this reagent has the capability to label only empty viral particles (i.e. empty and/or partially filled capsids) while fully packaged genomes (full capsids) remain unstained which may support techniques for rapid detection and/or quantification of viral particles. Thus, it is possible to selectively label the sample prior to processing the sample with the microfluidic device with a chemical agent such as gadolinium triacetate.

The inventors have recognized that selectively labeling only certain components of the sample may cause labeled components to respond differently to dielectrophoretic forces and/or electroosmotic forces applied to the sample. For example, selectively labeling the sample may increase a difference in mass between the labeled and unlabeled components (e.g., by increasing the mass of the labeled components). In some embodiments, selectively labeling the sample may increase a difference between the dielectric function of the labeled and unlabeled components. In some embodiments, selectively labeling the sample may increase a difference between the complex permittivity of the labeled and unlabeled components. The differences in response of the components to the applied DEP and/or EO forces may facilitate the detection, separation, purification, and/or quantification of viral particles and/or other components of the sample.

Following the optional labeling of the sample in act 212, process 200 may be complete. In some embodiments, the sample may be further prepared prior to processing in on the microfluidic system according to methods known in the art, and aspects of the present technology are not limited in this respect. In addition, it should be understood that one or more acts of the process 200 may be omitted.

(3) Example Microfluidic Systems

After preparing the fluid sample containing virus particles according to process 200, for example, the sample may be processed in a microfluidic system. For example, in a microfluidic device, the sample may be subjected to DEP forces and/or electroosmosis to enable rapid detection, separation, purification and/or quantification of viral particles in the fluid sample. Examples of a microfluidic system suitable for use in accordance with the techniques described herein, include the Fluid-Screen Microfluidic System, aspects of which are described in U.S. patent application Ser. No. 16/093,883 and titled "ANALYTE DETECTION METHODS AND APPARATUS USING DIELECTROPHORESIS AND ELECTROOSMOSIS," filed on Oct. 15, 2018, and U.S. patent application Ser. No. 14/582,525 and titled "APPARATUS FOR PATHOGEN DETECTION" filed on Dec. 24, 2014, each of which are hereby incorporated by reference in their entireties.

Figure 4:
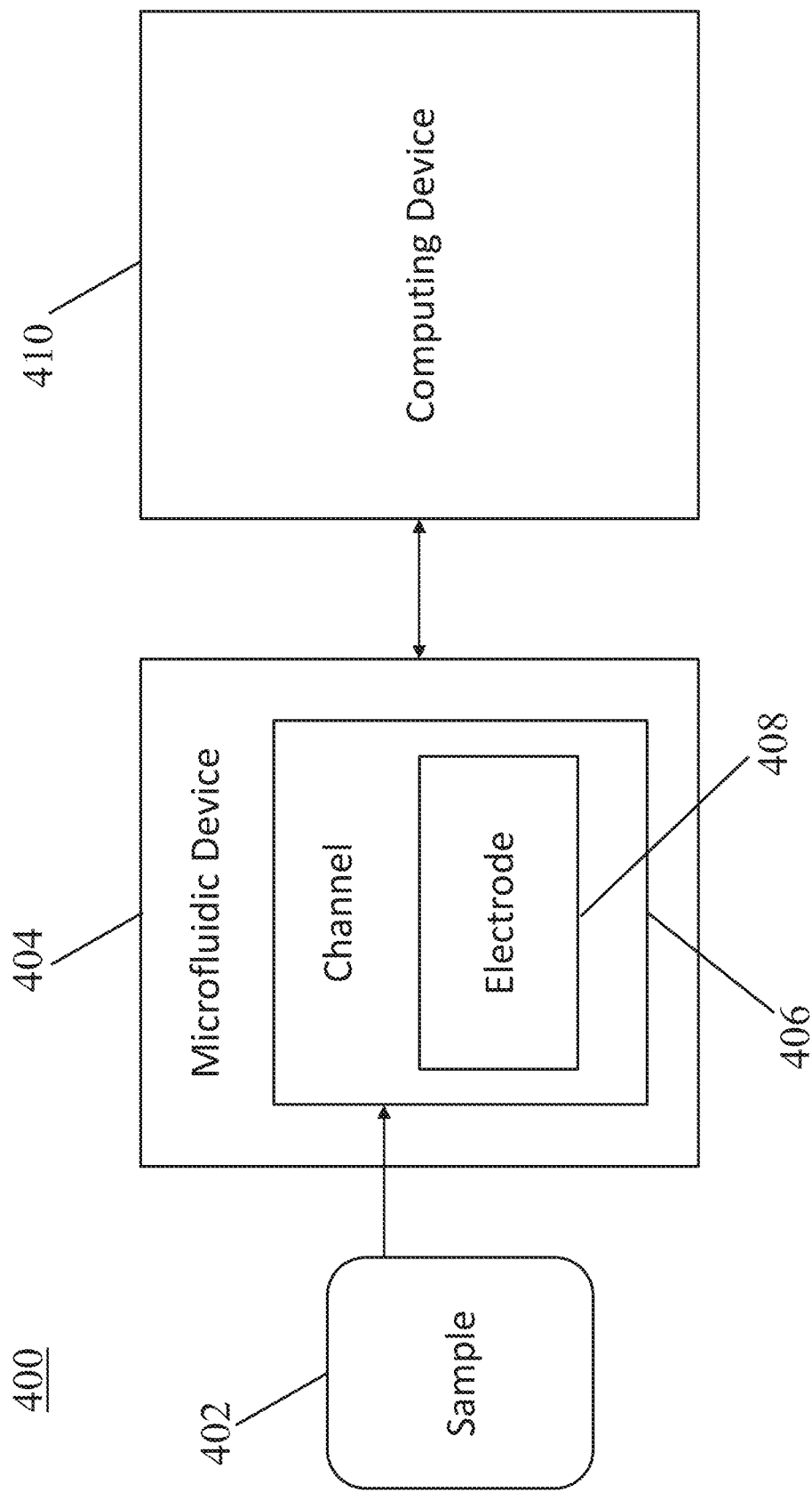
FIG. 4 illustrates an example system for rapidly detecting the presence of viral particles in a sample, according to some embodiments.

For example, FIG. 4 illustrates an example system for rapidly detecting the presence of viral particles in a sample, according to some embodiments. As shown in FIG. 4, the system 400 comprises a microfluidic device 404 in communication with a computing device 410.

Figure 6:
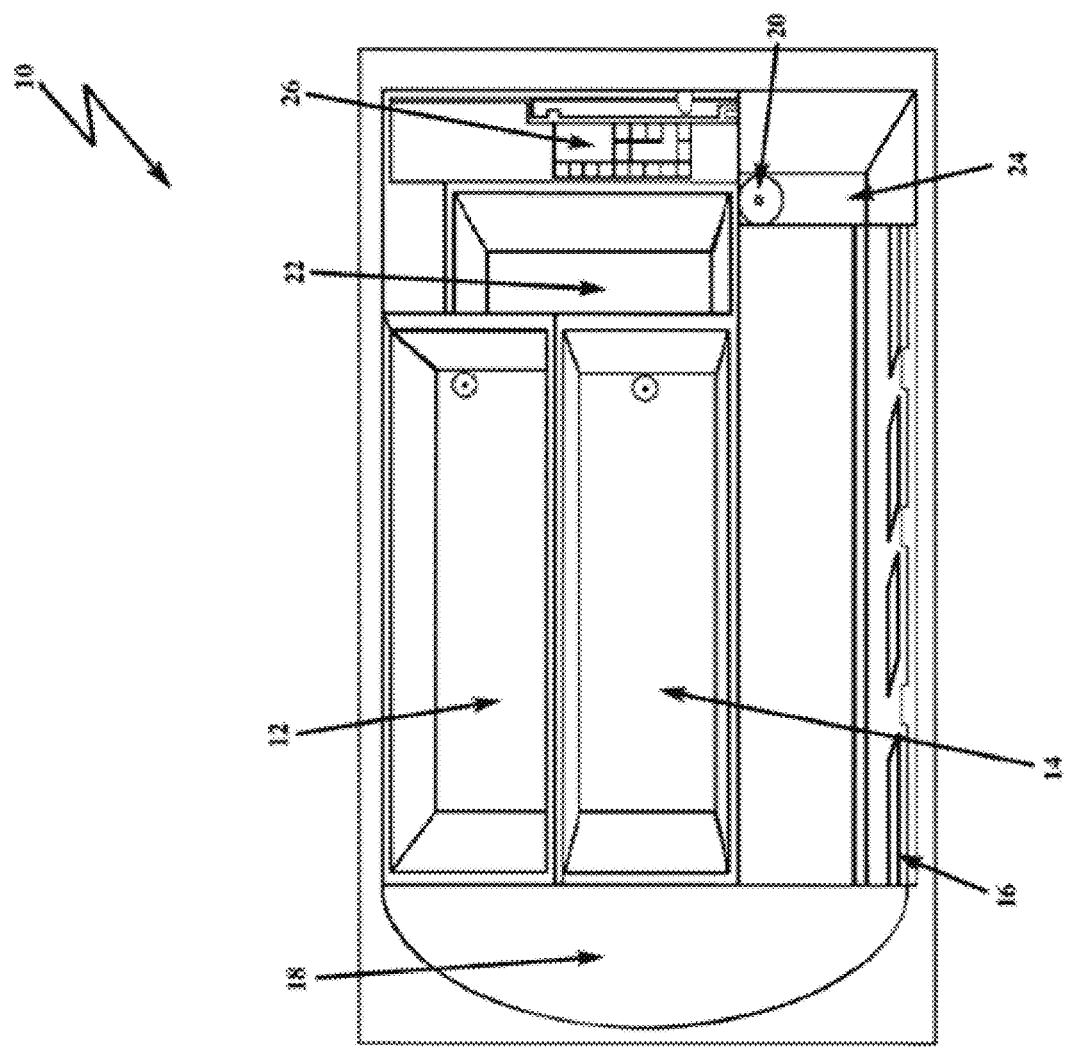
FIG. 6 illustrates an example microfluidic device for use in the example systems of FIGS. 4-5B, according to some embodiments.

The microfluidic device 404 may be any suitable device, examples of which are provided herein, in particular, with respect to FIG. 6. In the illustrated embodiment, the microfluidic device 404 comprises a channel 406 for receiving a sample 402 to be analyzed. Although, in the illustrated embodiment, the microfluidic device 404 comprises only a single channel 406, it should be understood that the microfluidic device 404 may comprise multiple channels 406, for receiving multiple samples. In such embodiments, the microfluidic device may process multiple samples in parallel (e.g., at the same or substantially the same time).

As described herein, the sample 402 may be any fluid which may contain viral particles. In some embodiments, the sample comprises a biological fluid such as saliva, urine, blood, water, or any other fluid such as an environmental sample or potentially contaminated fluid, etc.

The channel 406 may comprise at least one electrode 408. The at least one electrode 408 may be configured to generate at least one positive and/or negative dielectrophoretic force that acts on the sample. In some embodiments, the at least one electrode 408 may be configured to generate at least one electroosmotic force that acts on the sample. The at least one DEP and/or EO forces may cause certain components of the sample to move along the at least one electrode 408. For example, in the absence of an electric field, viral particles and other components of the sample 402 may be free to move in and out of focus. The small size of viral particles presents an obstacle to optical observation and quantification of the viral particles. The inventors have recognized that application of an electric field applied to the microfluidic device 404 may be used to trap viral particles on the surface of the electrode and/or the microfluidic device surface. The electric field capturing of the virus prevents viral particles from moving in and out of focus such that real-time virus detection and quantification may be performed.

The electric field which captures the viral particles further concentrates the viral particles. Concentrated viral particles, in the aggregate, emit fluorescence of higher intensity that may be more easily detected with optical method relative to individual viral particles. Thus, viral capture using an electric field as described herein allows for virus detection and quantification at significantly lower limits of detection than conventional methods. The ability to detect and/or quantify viral particles in a sample, even in small amounts, may be relevant in applications of biomanufacturing, gene therapy, analysis of patient samples, vaccine development and/or biothreat detection.

For example, the at least one DEP and/or EO forces may cause viral particles to separate from other components of the sample. Viral particles may accumulate on the surface of the at least one electrode 408 allowing for enhanced detection and/or quantification, despite the small size of the viral particles. Although, in the illustrated embodiment, the microfluidic device 404 is shown having only one electrode, it should be understood that in some embodiments, the microfluidic device 404 may comprise multiple electrodes. The at least one electrode(s) 408 may have any suitable shape. Examples of electrode shapes and designs are further described herein, in particular, with respect to FIGS. 12-16.

The system 400 may further comprise a computing device 410 for controlling the microfluidic device. For example, the computing device 410 may be configured to direct the sample 402 into the channel 406 of the microfluidic device having the at least one electrode 408. In some embodiments, the computing device 410 may be configured to control the at least one electrode 408 to generate the at least one DEP force and/or EO force acting on the sample 402. In some embodiments, the computing device 410 may cause one or more components of the microfluidic system (e.g., with an optical device) to perform the detection, quantification, separation, and/or purification of the viral particles/sample. Example computing devices are further described herein, for example, with respect to FIG. 17.

Figure 5A:
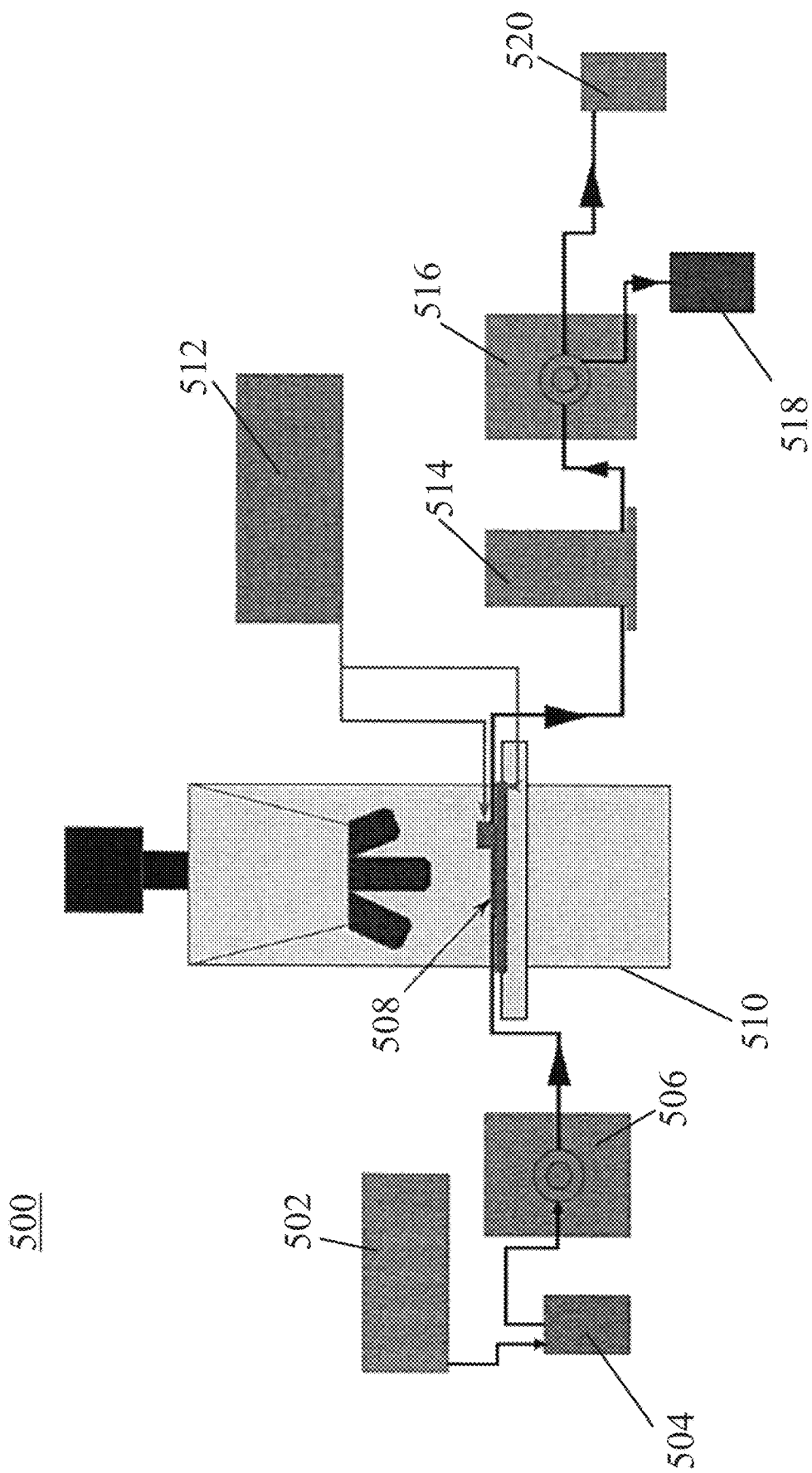
FIG. 5A illustrates an example electronic system for rapidly detecting the presence of viral particles in a sample, according to some embodiments.

FIG. 5A illustrates an example electronic system for rapidly detecting the presence of viral particles in a sample, according to some embodiments. The electronic system 501 comprises a microfluidic device 508, as described herein, for generating DEP and/or EO forces that act on a sample 504. The sample may contain viral particles for which detection, separation, purification, and/or quantification may be performed.

As shown in FIG. 5A, a flow system 502 is provided. The flow system 502 may provide a solution for transporting the sample 504 to the microfluidic device 508. A first pump 506 may be used to pump the solution and the sample 504 containing viral particles therein to the microfluidic device 508. The first pump 506 may be of any suitable type. In some embodiments, as further described herein, the first pump 506 is omitted, and the sample 504 is manually loaded onto the microfluidic device 508.

The microfluidic device 508 receives the sample 504 for analysis. As described herein, the microfluidic device 508 may be configured having a channel containing at least one electrode for generating an applied electric field that acts on the sample 504. An electrical system 512 may provide voltage to the at least one electrode of the microfluidic device 508. Further aspects of the electrical system 512, including example protocols for operating the microfluidic device 508 are provided herein.

An optical system 510 may be provided to facilitate analysis of the sample 504. For example, the optical system 510 may comprise one or more optical sensors for viewing and/or imaging the sample. The optical sensor(s) may provide for enhanced detection and/or quantification of the viral particles and/or the other components of the sample 504. Any suitable optical detector may be used. In some embodiments, the optical sensor(s) comprises a digital camera. In some embodiments, the optical sensor(s) comprises electronic sensors made of nanowire and/or nanoribbon technology. However, any suitable optical sensor(s) may be used.

After sufficient analysis of the sample 504 is performed by the microfluidic device 508 and/or optical system 510, the sample 504 may be unloaded from the microfluidic device 508. For example, a second pump 516 may be provided for pumping the sample 504 away from a surface of the at least one electrode of the microfluidic device 508. The second pump 516 may be of any suitable type. In some embodiments, the system 500 comprises a flow sensor 514 for measuring a flow rate at which the sample 504 is removed from the microfluidic device 508. The flow sensor 514 and the second pump 516 may be in communication to control a flow rate at which the sample 504 is removed from the microfluidic device 508.

As described herein, the system 500 may be used for purifying a sample 504 containing viral particles. Thus, in some embodiments, the system 500 comprises a waste region 518 for receiving other components of the sample 504 which have been separated from the viral particles by the microfluidic device 508 and subsequently removed from the sample 504 using the second pump 516. The system 500 may further comprises an effluent region 520 for receiving the purified sample 504 containing substantially only viral particles. In some embodiments, the other components comprise empty and/or partially filled capsids and the viral particles comprise substantially only full capsid particles. Thus, purifying the sample 504 using the microfluidic device 508 comprises separating the empty and/or partially filled capsids from the full capsid viral particles of the sample 504 using DEP and/or EO forces generated by the at least one electrode, and removing the empty and/or partially filled capsids from the sample 504 to be disposed of in a waste region 518 via the second pump 516 while the viral particles of the sample 504 are transported to an effluent region 520. However, in some embodiments, both full capsid viral particles and empty and/or partially filled capsids are transported to the effluent region 520 and no particles are transported to the waste region 518. In some embodiments, all of the sample 504 is transported to the was region 518 and no particles are transported to the effluent region 520.

As described herein, in some embodiments, the sample 504 may be manually loaded onto the microfluidic device 508 for analysis. For example, FIG. 5B illustrates an example manual system 501 for rapidly detecting the presence of viral particles in a sample, according to some embodiments. The manual system 501 may omit certain components of the electronic system 501, such as the first pump 506.

An example microfluidic device for receiving a sample containing viral particles is shown in FIG. 6, which is reproduced from U.S. patent application Ser. No. 13/664,967, now U.S. Pat. No. 9,120,105, entitled "ELECTRONIC DEVICE FOR PATHOGEN DETECTION" filed on Oct. 31, 2013, which is hereby incorporated by reference in its entirety. Device 10 in FIG. 6 comprises a sample chamber 12 and a chamber 14 containing a reference solution which may in some embodiments include a separator which purifies the reference solution from contaminants. In some embodiments, the device 10 may not include the chamber containing the reference solution.

The chambers 12 and 14 are connected by micropumps adapted to force either fluid around the passage 18 and through separator passage 16. First, the sample comprising viral particles and other components may be pumped through the separator. The separator applies a dielectrophoretic, electroosmotic, and/or AC kinetic force on the components of the sample tending to draw the viral particles towards the bottom of the figure and the other components, which may, in some embodiments, be subsequently disposed of towards the top. The other components may be trapped in chamber 22, while the viral particles are drawn into the holding chamber 24 by concentrator 20, which the separator and the condenser may in some embodiments comprise a set of coaxial interdigitating rings or arches having independent voltages. Once the viral particles are held by the concentrator 20, the buffer solution may be pumped from chamber 12 around the bend 18 and through the separator passage 16 to flush the chamber 24, effectively changing the medium in which the viral particles are found and eliminating any residual unfiltered elements. The viral particles can then be released from concentrator 20 (by removing the electric field) and drawn towards analyzer array 26 (which itself is provided with DEP electrodes adapted to draw the analyte thereto).

The device uses dielectrophoresis for purposes of separating viral particles from other components of a sample. Dielectrophoresis uses a natural or induced dipole to cause a net force on a particle in a region having an electric field gradient.

$$F=2\pi\epsilon_m R^3 \text{Re}[\underline{CM}(\omega)\cdot\nabla\underline{E}^2(r,\omega)]$$

This force depends on the Clausius-Mossotti factor CM(w) defined by $$CM(\omega) = \frac{\epsilon_p^o - \epsilon_m^o}{\epsilon_p^o + 2\epsilon_m^o}$$

where $\epsilon^o$ is the complex permittivity, $$\epsilon^o = \frac{\sigma}{i\omega}.$$

In some embodiments, the values for a and w are chosen to reach a maximal separation force between the analyte and other elements in the incoming solution being tested. This can be accomplished by compiling knowledge concerning both the viral particles and other components to be separated. The differential response of the viral particles and other components of a sample can be inspected for its extrema which will show the greatest differential response tending to separate the viral particles from the other components. The frequency for maximal separation is easily effected (this being the frequency of the applied field), while the conductivity of the solution can be controlled by titration of a known amount of solution of known conductivity (or equivalently, salinity). Alternatively a feedback technique may be used by measuring the conductivity of the solution and adding saline or deionized water (for instance) until a desired conductivity is reached. A reference measurement may be used for quality control and identification of the solution. A differential measurement of the control signal (no contamination) with an actual signal (with labeled contaminants) may be used. Conductivity and complex permittivity measurements may be implemented at multiple stages in the devices for quality control of fluid mixing and feedback adjusting the mixing rate.

As will be appreciated by one skilled in the art, such analysis of a differential response may be performed any pair of species in question in a given sample. In one embodiment, a microfluidic chamber having electrodes has an applied electric field of such frequency that the response of protein structures in a fluid sample processed on the microfluidic system is differential compared to the response of protein structures that form an empty capsid, thereby separating empty capsids from fully packaged genomes. Furthermore, successive filtration acts can be taken to maximize separation, for example, by taking successive filtration acts to separate different substances in each act from each other.

(4) Example Techniques

As described herein, a microfluidic device may be used to perform rapid detection, separation, purification, and quantification of viral particles in a sample. Example techniques for performing such rapid detection, separation, purification, and quantification are now provided herein.

Figure 7:
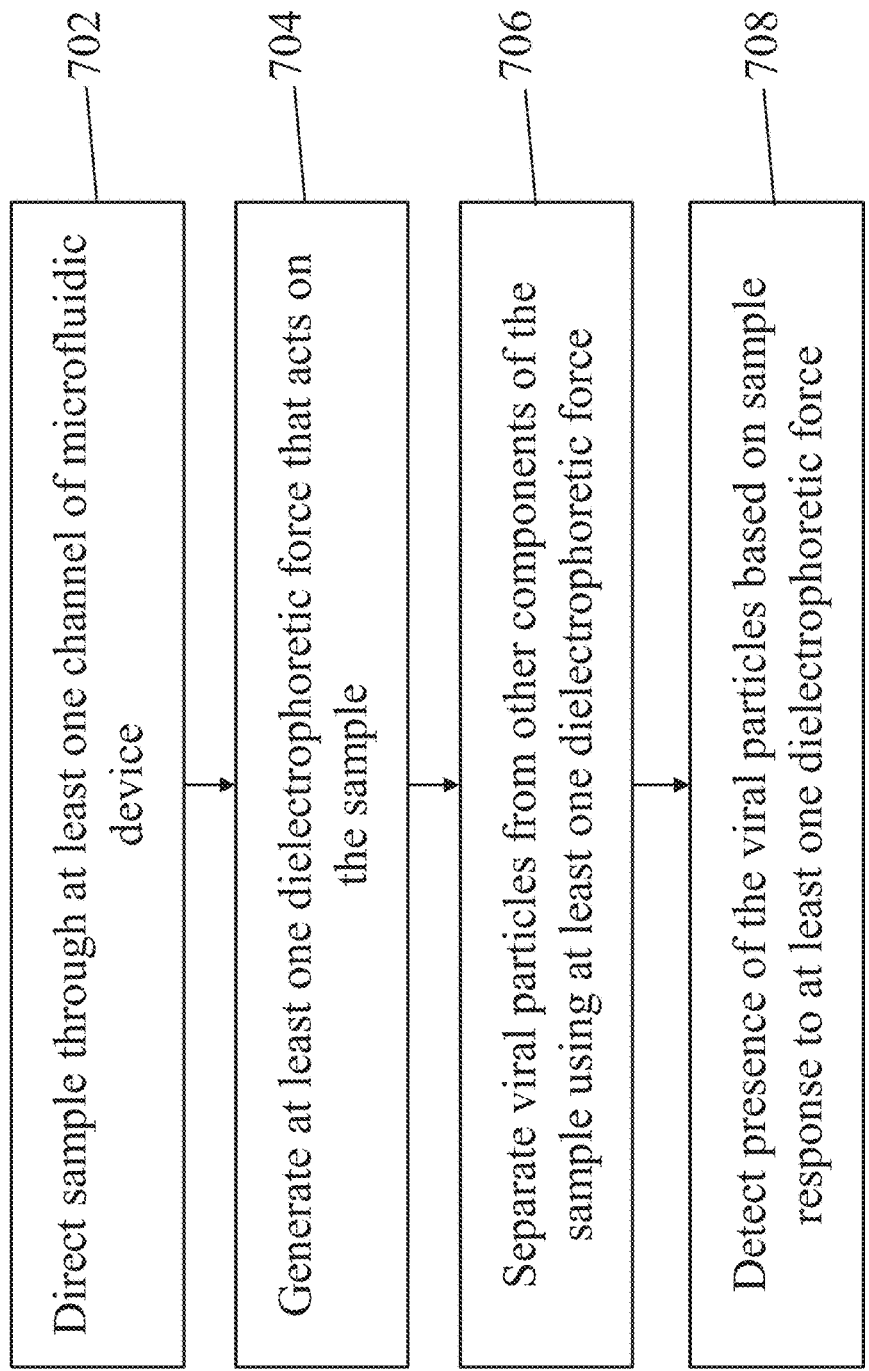
FIG. 7 illustrates an example process for rapidly detecting the presence of viral particles in a sample, according to some embodiments.

FIG. 7 illustrates an example process for rapidly detecting the presence of viral particles in a sample, according to some embodiments. The example process 700 begins at act 702, where a sample which may contain viral particles is directed through at least one channel of a microfluidic device, such as the microfluidic devices described herein. In some embodiments, the microfluidic device comprises a plurality of channels, and a plurality of samples are processed by the microfluidic device in parallel (e.g., at the same or substantially the same time).

The at least one channel may comprise an electrode for generation DEP and/or EO forces which act of the sample. Thus, at act 704, at least one dielectrophoretic force that acts on the sample is generated using the electrode of the microfluidic device. The at least one DEP force may cause components to move in a particular manner (e.g., in a particular direction, at a particular velocity, with a particular trajectory, etc.). In some embodiments, the movement of the sample components in response to the applied DEP force may be indicative of the type of component in the sample (e.g., a viral particle or other component). In some embodiments, motion characteristics of the sample components may be used to identify the sample components. Although not shown in FIG. 7, the process 700 may additionally or alternatively include generating at least one EO force acting on the sample components.

The DEP force generated at act 704 and acting on the sample may cause different components of the sample to separate due to differential response of the sample components to the DEP force. For example, the applied DEP force may cause viral particles to accumulate in first region on the surface of the electrode while other components accumulate in a second region on the surface of the electrode. Separating the viral particles of the sample from other components may facilitate visual detection of the viral particles. As such at act 706, the viral particles are separated from other components of samples due to the at least one DEP force acting on the sample.

At act 708, the presence of viral particles may be detected. As described herein, viral particles are difficult to detect, due to their small size (e.g., having a diameter of 400 nm or less) and ability to flow freely in a sample. The inventors have recognized that DEP and/or EO forces may be used to immobilize and aggregate the viral particles in a region on the surface of the electrode. The accumulation of the viral particles may reduce the difficulty of detecting individual viral particles. In some embodiments, detecting the presence of the viral particles is performed using an optical sensor, as described herein.

Figure 8A:
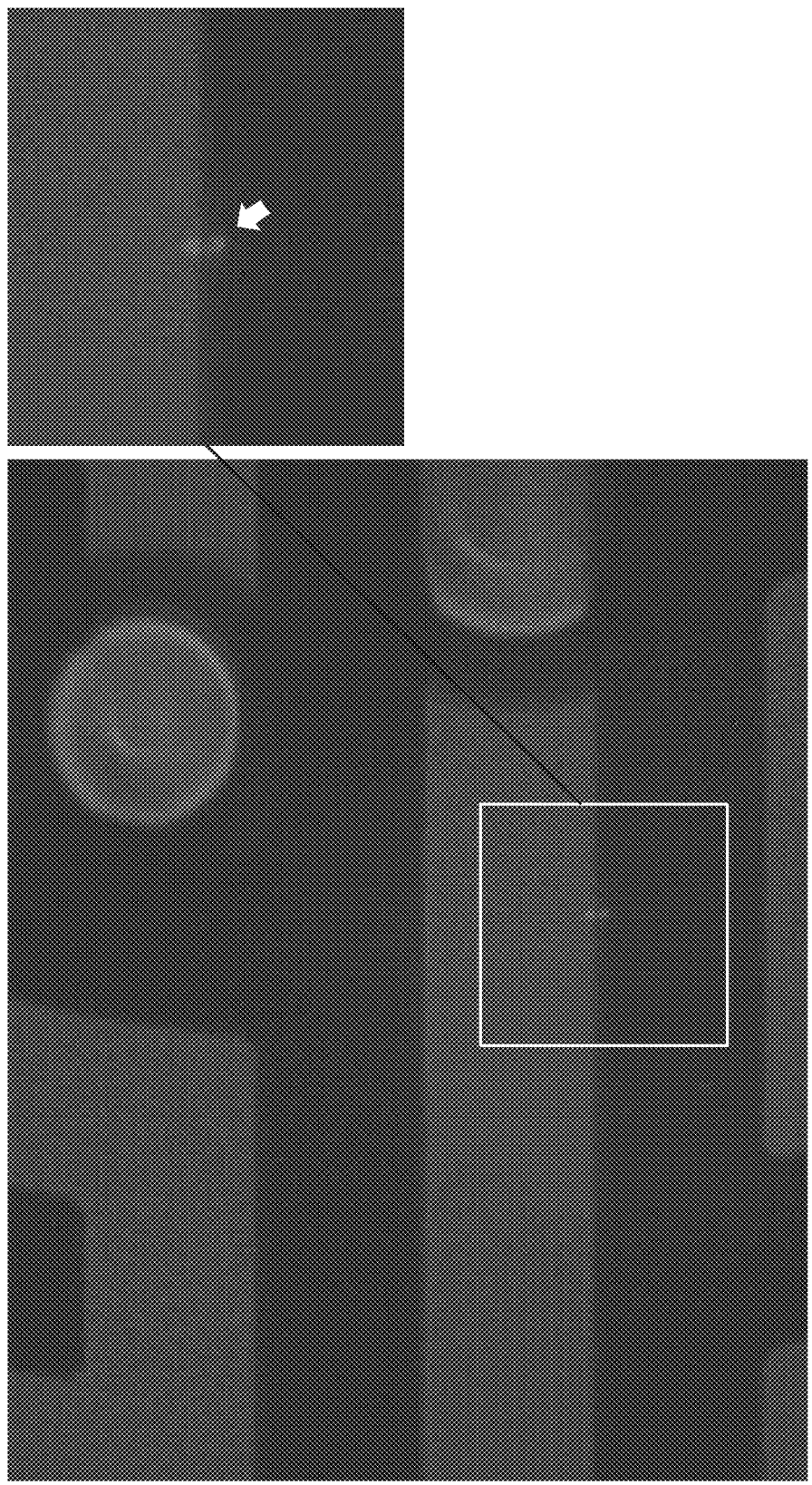
FIGS. 8A-C show examples of dielectrophoretic captures of viral particles concentrated on the surface of electrodes in a microfluidic system, according to some embodiments.
Figure 8B:
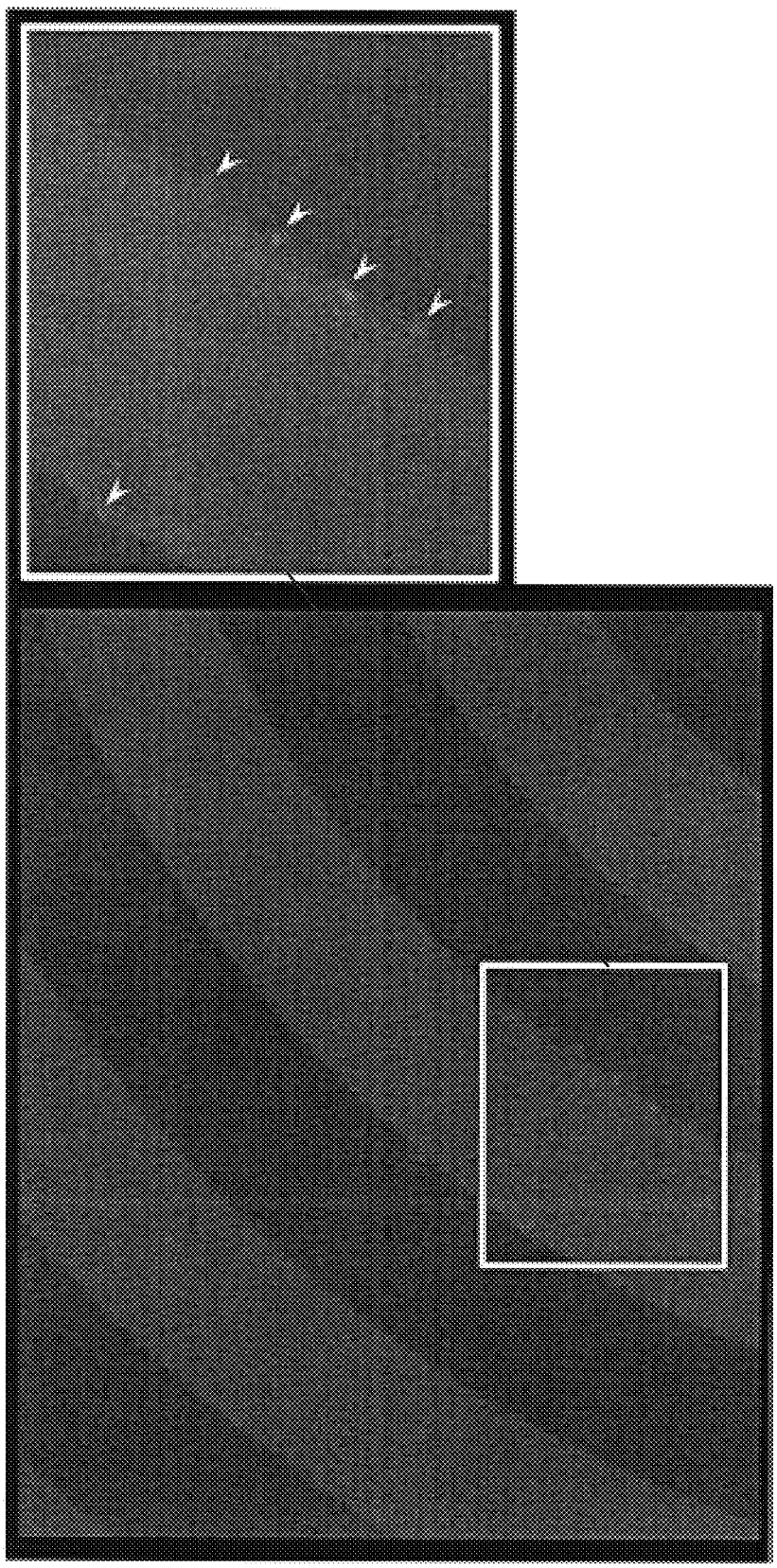
Figure 8C:
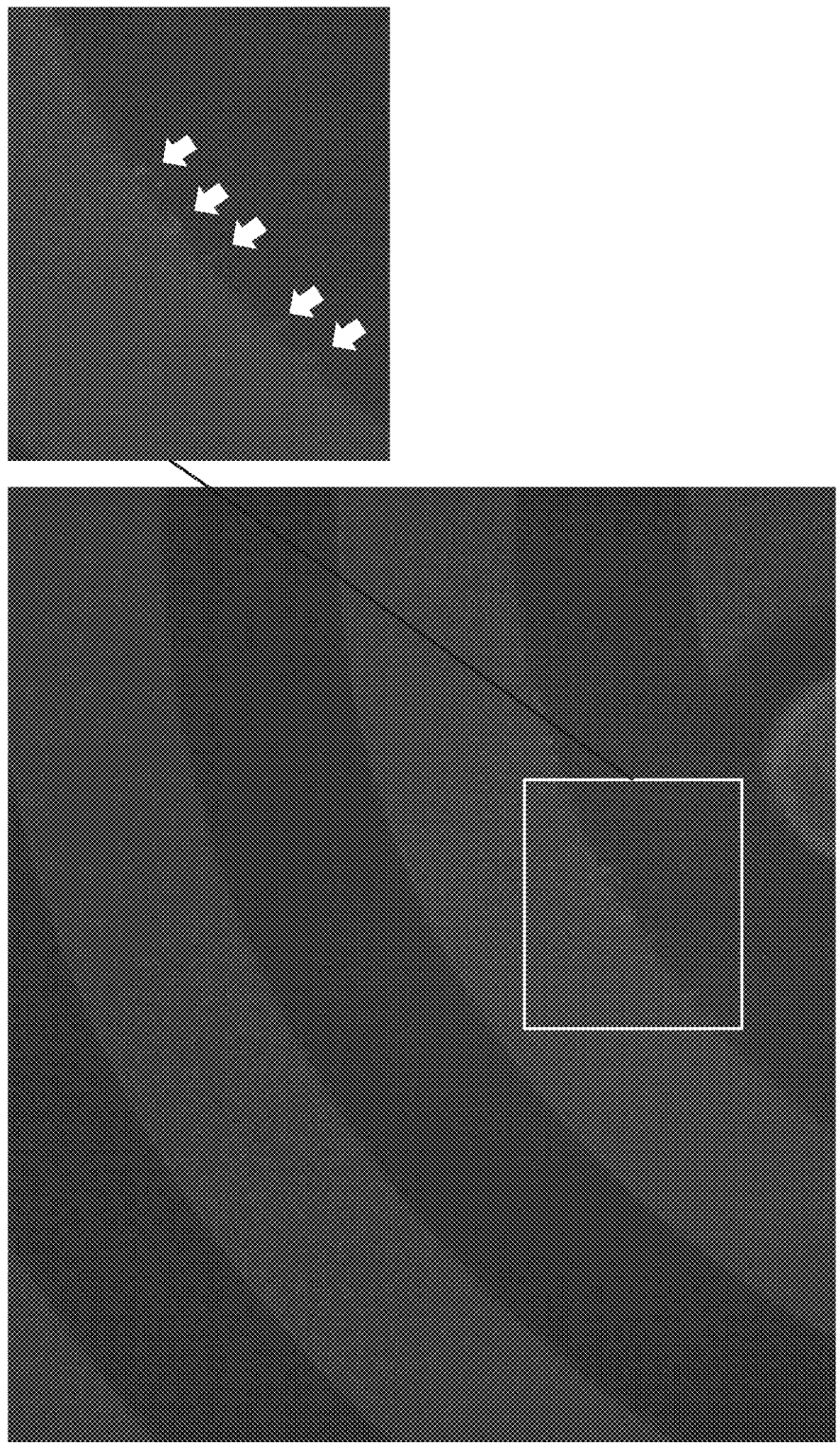

FIGS. 8A-C show examples of dielectrophoretic captures of viral particles concentrated on the surface of electrodes in a microfluidic system, according to some embodiments. As described herein, the small size of such viral particles presents a challenge for rapid detection and/or quantification. By utilizing the microfluidic system in combination with DEP and/or electroosmosis, unstained, stained and/or differentially stained viral particles can be more easily quantified.

For example, in the absence of an electric field, virus particles are free to move in and out of focus. When an electric field is applied to the electrode system of the microfluidic chamber, viral particles become trapped on a surface of an electrode of the electrode system thus preventing virus particles from moving in and out of focus. By capturing viral particles on the electrode surface, the microfluidic system concentrates virus particles into a region. Concentrated virus particles, in the aggregate, emit fluorescence of higher intensity. For example, in FIGS. 8A-C, dielectrophoretic captures of viral particles concentrated on electrodes a microfluidic system are shown. FIGS. 8A-C show a visible accumulation of viral particles, given the relatively higher intensity fluorescence emitted from the concentrated particles.

Concentrated virus particles emitting fluorescence may then be recorded through optical methods. The inventors have recognized that optical capture of concentrated viral particles may be achieved by various methods known in the art, and aspects of the technology are not limited in this respect. Thus, application of an electric field in the system of electrodes to concentrate viral particles allows for rapid virus detection and quantification at a significantly lower limit of detection, which can be relevant in the context of biomanufacturing, gene therapy, analysis of patient samples, and biothreat detection.

Figure 9:
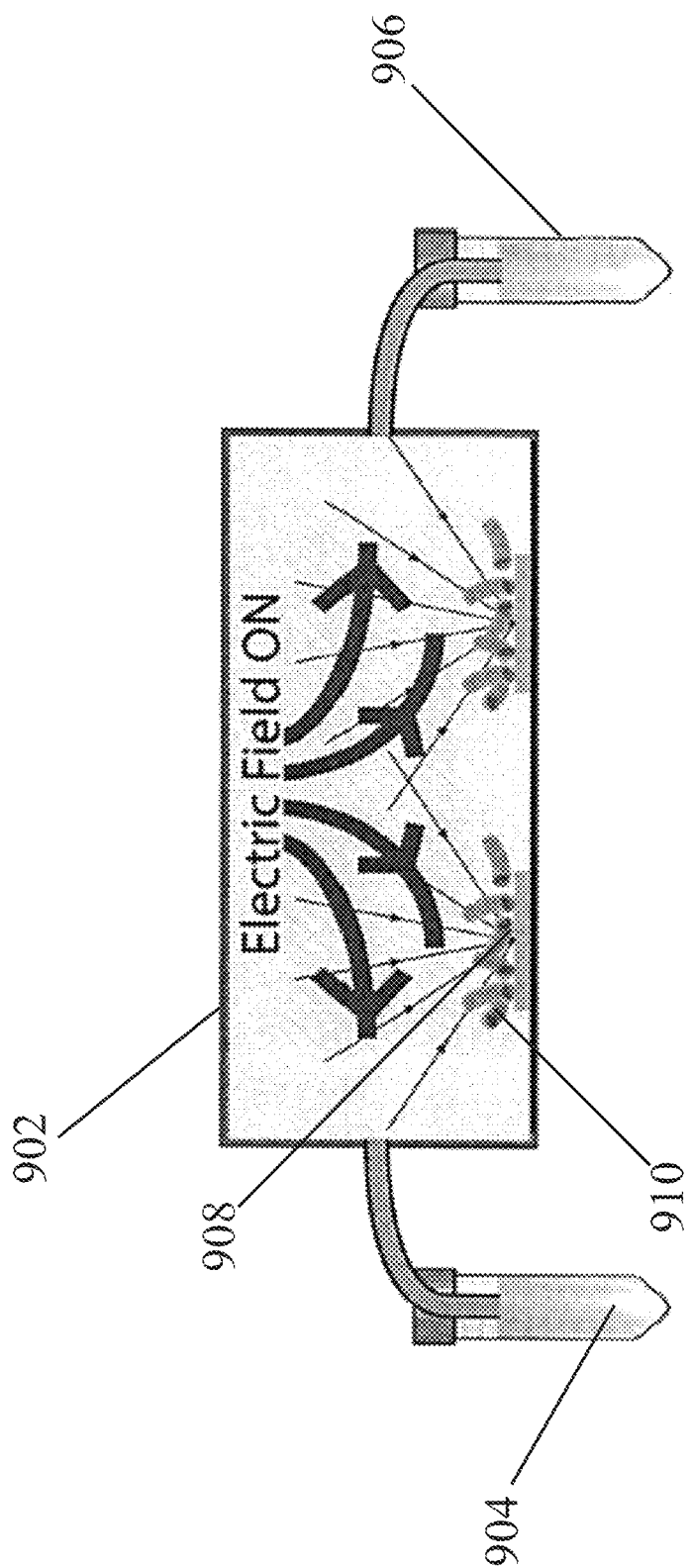
FIG. 9 illustrates an example schematic diagram of captured and release of viral particles on a static microfluidic device having electrodes, according to some embodiments.

FIG. 9 illustrates an example schematic diagram of captured and release of viral particles on a static microfluidic device having electrodes, according to some embodiments. FIG. 9 is a schematic illustration of the immobilization of sample components 910 (e.g., viral particles) on an electrode 908 of a microfluidic device 902. In particular, sample components may be introduced to the microfluidic device 902 from an influent region 904. Certain components of the sample may be trapped on the surface of one or more electrodes 908 due to an applied electric field. The electric field may be subsequently adjusted to release the sample components 910 to an effluent region 906.

Figure 10:
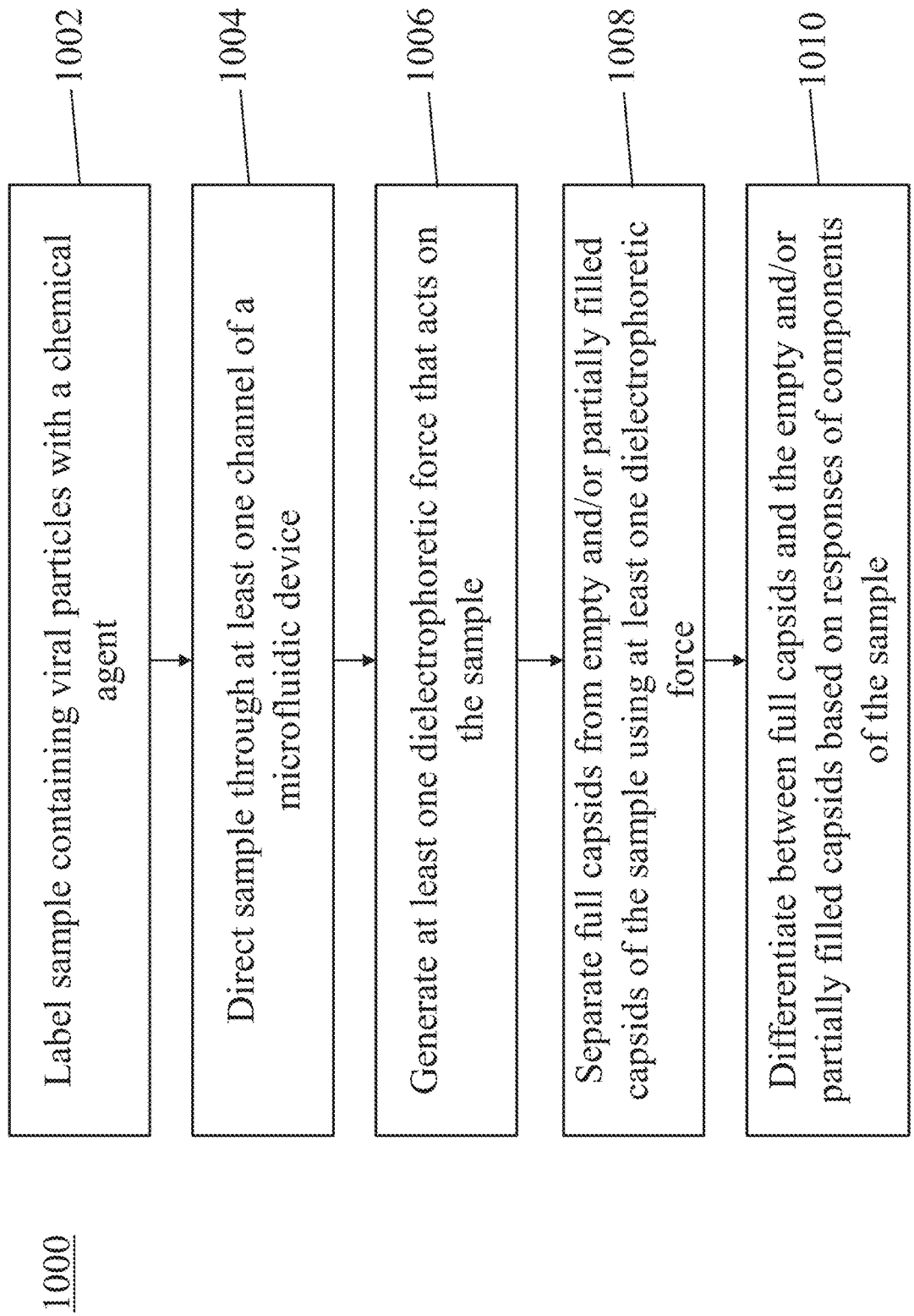
FIG. 10 illustrates an example process for differentiating between full capsid viral particles and empty and/or partially filled capsids, according to some embodiments.

FIG. 10 illustrates an example process for differentiating between full capsid viral particles and empty and/or partially filled capsids, according to some embodiments. Process 1000 begins at act 1002 where a sample containing viral particles is labeled with a chemical agent (e.g., gadolinium triacetate). The labeling at act 1002 may comprise selectively labeling the sample, such that only some components of the sample are labeled while others remain unlabeled. In some embodiments, selectively labeling the sample comprises labeling only the viral particles (e.g., full capsids) and not labeling the other components (e.g., empty and/or partially filled capsids). In some embodiments, selectively labeling the sample comprises not labeling the viral particles (e.g., full capsids) and only labeling the other components (e.g., empty and/or partially filled capsids). As described herein, the selective labelling may enhance a differential response of the components of the sample to applied DEP and/or EO forces.

At act 1004, the labeled sample is directed through at least one channel of a microfluidic device. For example, the at least one channel may comprise at least one electrode for generating at least one DEP and/or EO force that acts on the sample.

At act 1006, at least one DEP force that acts on the sample is generated by the electrode of the microfluidic device. As described herein, the at least one DEP force may cause components of the sample to move in a particular way. Due to the selective labeling performed at act 1002, the movement of the sample components in response to the applied DEP force may be different depending on whether the sample is labeled.

At act 1008 the applied DEP force causes the full capsid viral particles to separate from the empty and/or partially filled capsids. The selective labeling performed at act 1102 may enhance the differential response of the full capsid viral particles to the empty and/or partially filled capsids. For example, as described herein, selectively labeling the sample may increase a difference in mass between the labeled and unlabeled components (e.g., by increasing the mass of the labeled components). In some embodiments, selectively labeling the sample may increase a difference between the dielectric function and/or complex permittivity of the labeled and unlabeled components. Such differences may cause the labeled components to visibly respond differently to the applied DEP force(s). Furthermore, the inventors have recognized that the difference in reaction to DEP forces by labeled vs. unlabeled particles is applicable whether or not the sample comprises equal quantities of labeled and unlabeled components. Thus, the approach described herein does not require optimization of capsid-specific purification methods for each serotype which can enable large scale performance of virus purification.

At act 1008, the differential response of the labeled and unlabeled sample components allows for differentiating between full capsid viral particles and the empty and/or partially filled capsids. Differentiating between the full capsid viral particles and the empty and/or partially filled capsids may comprise detecting a presence of the full capsid viral particles and/or the empty and/or partially filled capsids. In some embodiments, the differentiating comprises quantifying the full capsid viral particles and/or the empty and/or partially filled capsids, and may further comprise determining a difference between an amount of full capsid viral particles and empty and/or partially filled capsids.

Figure 11:
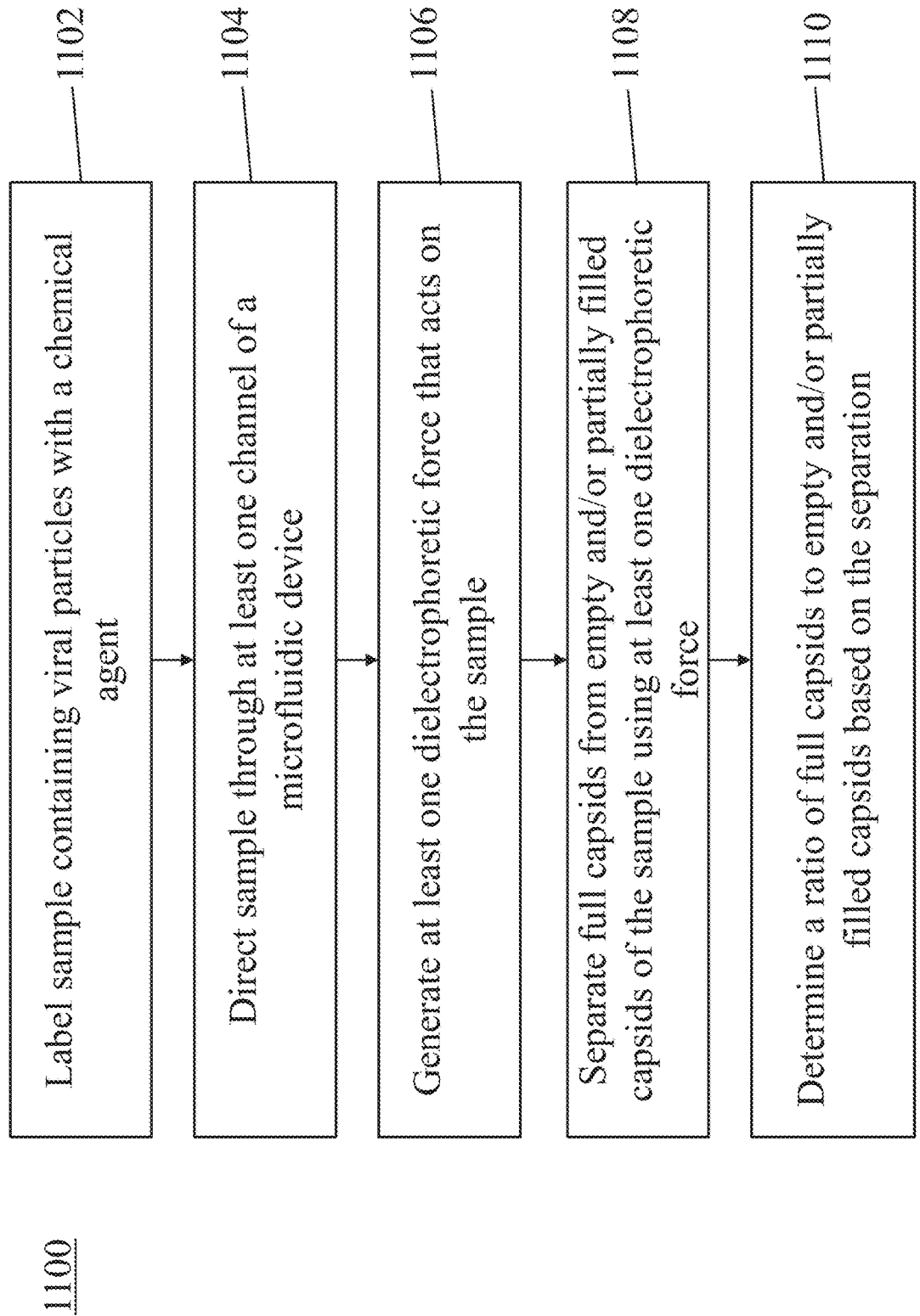
FIG. 11 illustrates an example method for determining a ratio of full capsid viral particles to empty and/or partially filled viral particles, according to some embodiments.

FIG. 11 illustrates an example method for determining a ratio of full capsid viral particles to empty and/or partially filled viral particles, according to some embodiments. Acts 1102-1108 of process 1100 are similar to those described in acts 1002-1008 of process 1000. For example, at act 1102, a sample containing viral particles is labeled with a chemical agent (e.g., gadolinium triacetate). At act 1104, the labeled sample is directed through at least one channel of a microfluidic device. At act 1106, at least one dielectrophoretic force that acts on the sample is generated by at least one electrode of the microfluidic device. At act 1108, the generated dielectrophoretic force causes full capsid viral particles to separate from empty and/or partially filled capsids.

Process 1100 then proceeds to act 1100, where a ratio of full capsids to empty and/or partially filled capsids is determined. Determining the ratio of full capsids to empty and/or partially filled capsids may be performed using an optical sensor, for example, a digital camera. As described herein, the determined ratio may be reported, as required, in some contexts, and/or the determined ratio may be used to optimize a drug manufacturing process by making adjustments to the manufacturing process to adjust the ratio of full capsids to empty and/or partially filled capsids.

(5) Electrode Designs and Additional Device Functionality

As described herein, the techniques for rapidly detecting, separating, purifying and/or quantifying viral particles in a sample may be performed using a microfluidic device having a channel with at least one electrode. The at least one electrode may have any suitable shape and design. In some embodiments, for example, the at least one electrode comprises at least one circular-shaped and/or partially-center-symmetric electrode. Example electrode designs are provided in FIGS. 12-16H herein.

Figure 12:
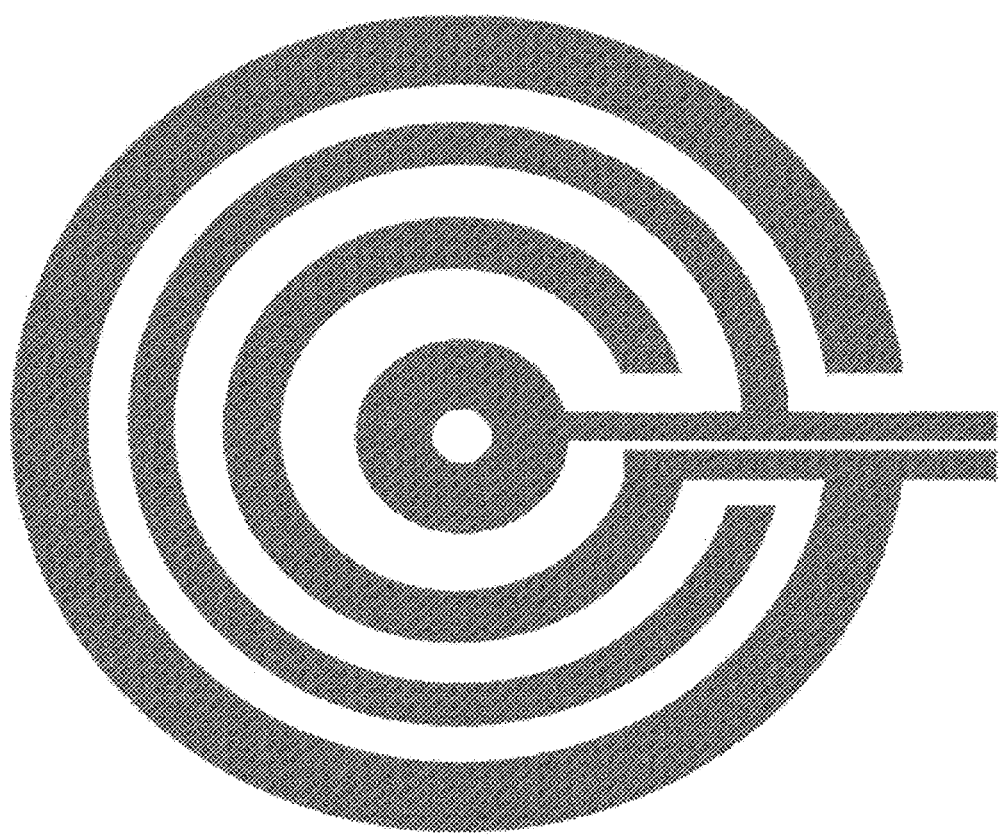
FIG. 12 illustrates a circular assembly of electrodes that may be used in accordance with some embodiments of the technology described herein.

For example, some embodiments make use of a circular assembly of coaxial or spiral-shaped electrodes such as shown in FIG. 12, where two or more independent voltages may be applied to the odd and even rings. This allows for an electric field gradient to be created in the region between the rings. The assembly of electrodes is constructed in such a way as to maximize the effects of the electric field on controlling the motion of the sample components.

Figure 13:
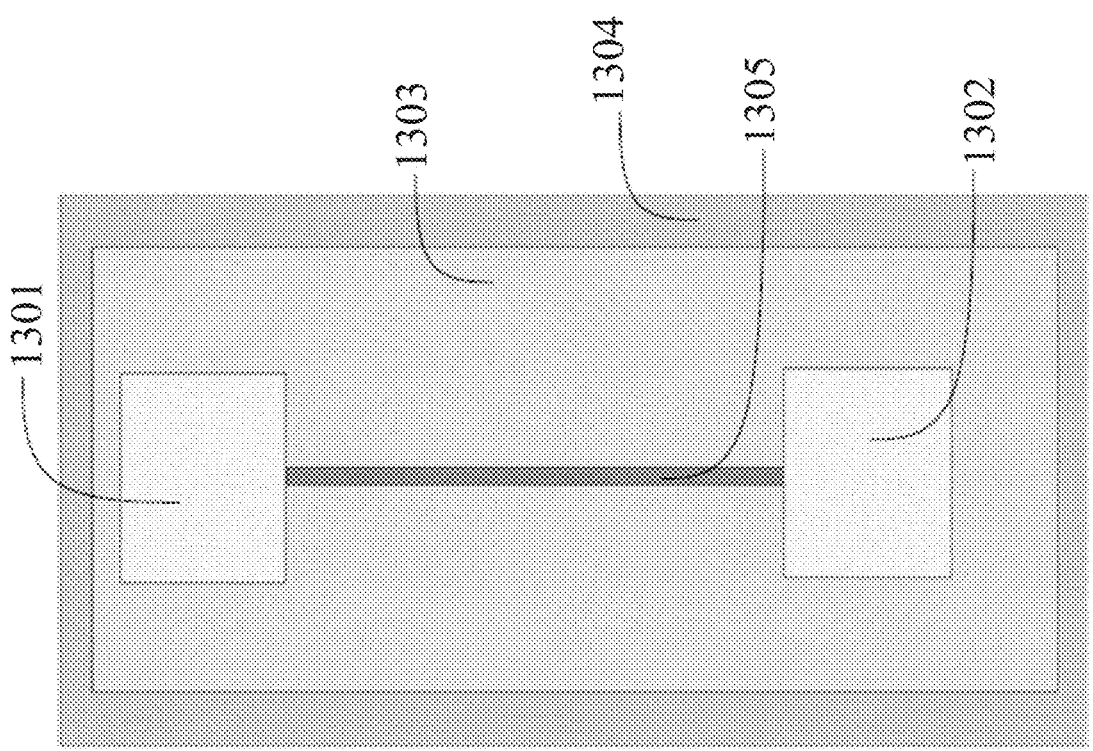
FIG. 13 illustrates a sensor assembly that may be used in combination with the electrode assembly of FIG. 12, according to some embodiments.

Such a device may be used to draw components of a sample, e.g. viral particles, or other elements to the sensor array, which may be composed of elements such as those shown in FIG. 13, namely source 1301 and drain 1302, nanowire, nanoribbon or active sensing layer 1305, silicon or other semiconducting substrate 1304 and $SiO_2$ or other insulating interlayer 1303.

Figure 14:
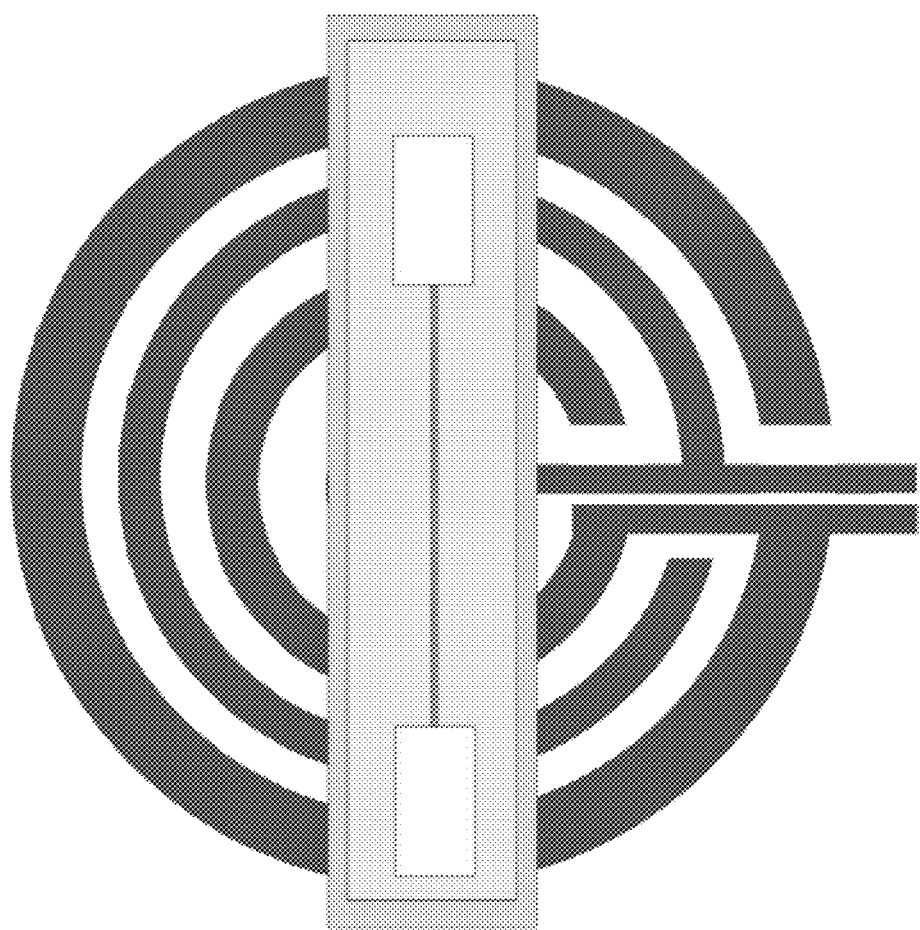
FIG. 14 illustrates the sensor assembly of FIG. 13 fabricated on top of the circular electrode assembly of FIG. 12, according to some embodiments.
Figure 15A:
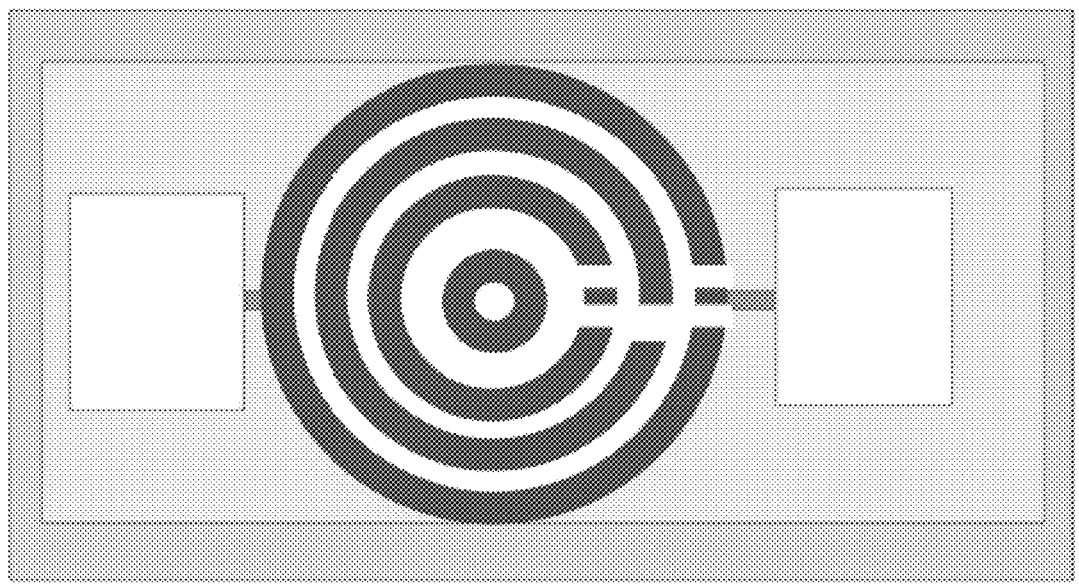
FIG. 15A illustrates the circular electrode assembly of FIG. 12 fabricated on top of the sensor assembly of FIG. 13, according to some embodiments.
Figure 15B:
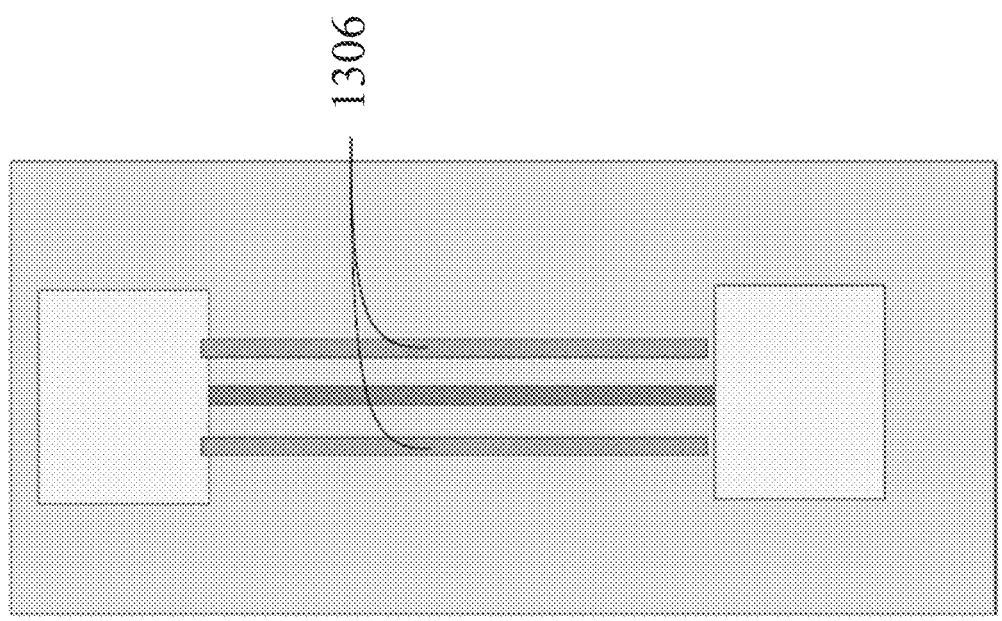
FIG. 15B illustrates an example device that includes supplementary wires arranged to provide a field gradient in a region of a central sensing layer, according to some embodiments.

The sensor assembly of FIG. 13 may be fabricated on top of circular DEP electrodes as shown in FIG. 14, or a set of circular electrodes may be fabricated on top of (or underneath, in some embodiments) the $SiO_2$ or other insulating layer as shown in FIG. 15A. Alternatively, two supplementary wires 1506 may be used as shown in FIG. 15B to provide a field gradient in the region of the central sensing layer.

A further aspect allows for selective treatment of individual sensors in a sensor array, such that each sensor or group of sensors can be made sensitive to a particular pathogen or family of pathogens. The sensor array may be such as that disclosed in U.S. patent application Ser. No. 12/517,230 titled "CMOS-COMPATIBLE SILICON NANO-WIRE SENSORS WITH BIOCHEMICAL AND CELLULAR INTERFACES" filed on Jul. 12, 2010, which is hereby incorporated by reference in its entirety. In some embodiments, the wires of the array form the bases of field-effect transistors, and thus implement nanowire FETs or FETs.

Figure 16A:
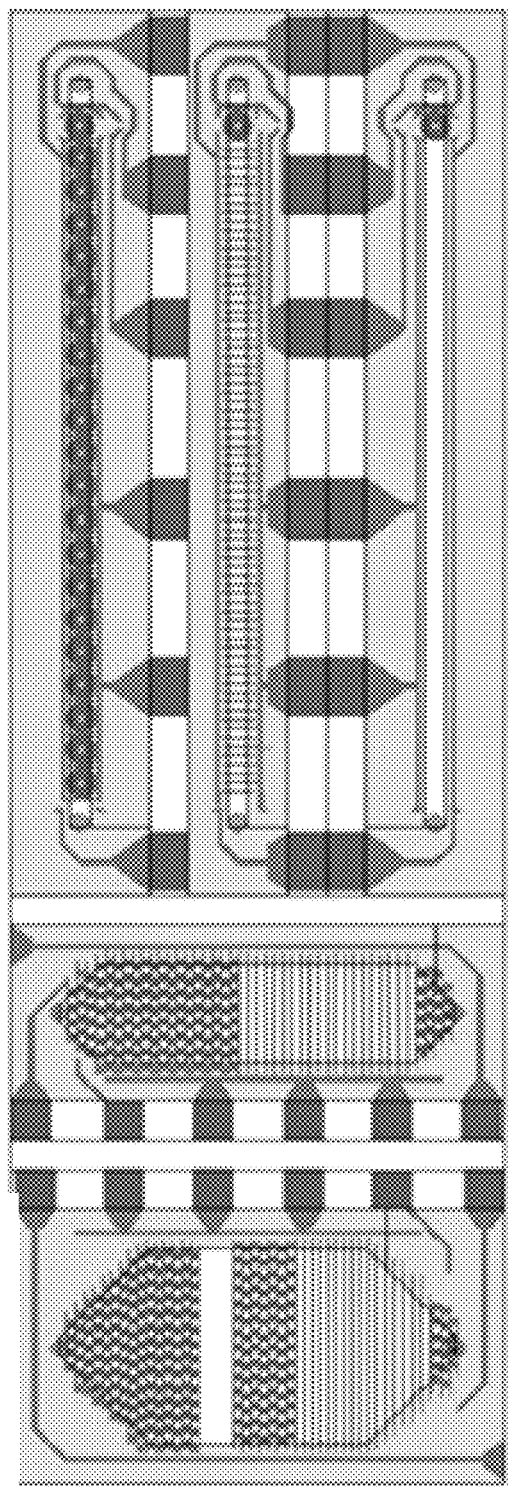
FIG. 16A illustrates a layout for an example microfluidic device, according to some embodiments.
Figure 16B:
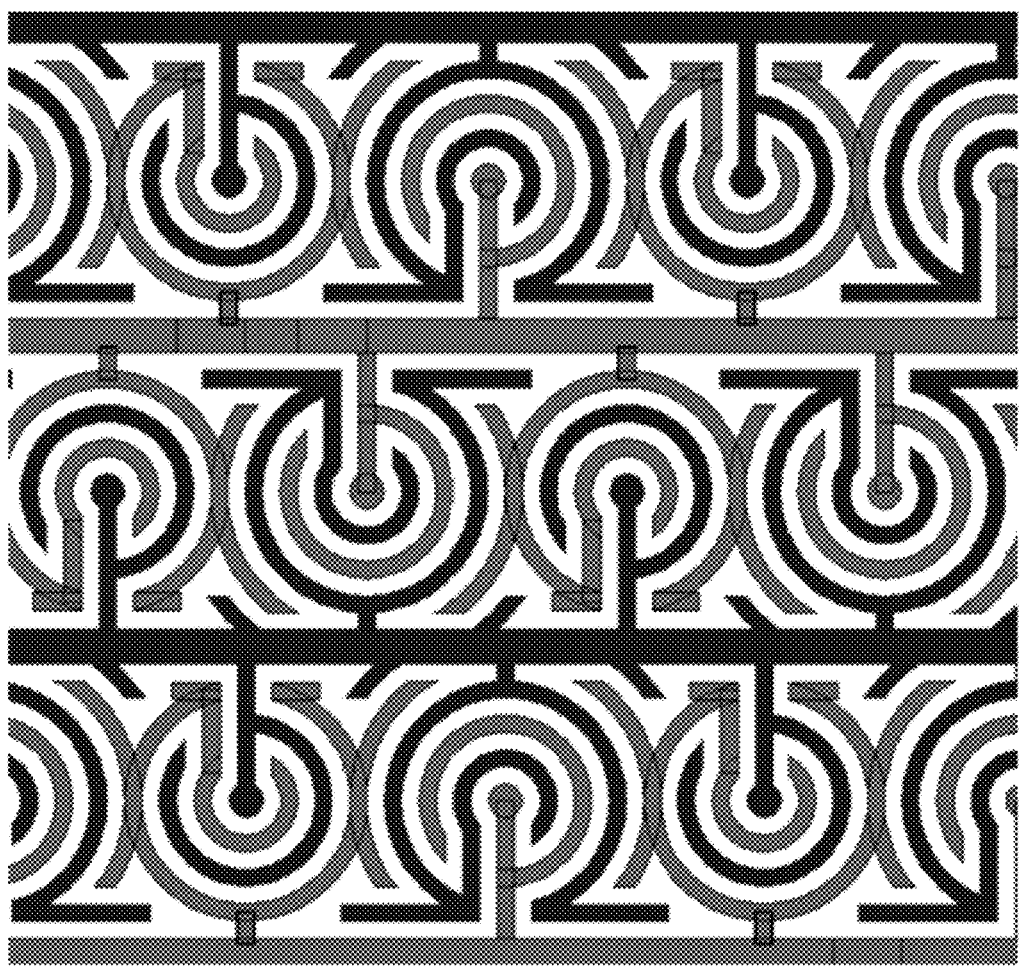
FIGS. 16B-H illustrate different geometries of electrodes for high surface coverage to achieve high electric field gradients, according to some embodiments.
Figure 16C:
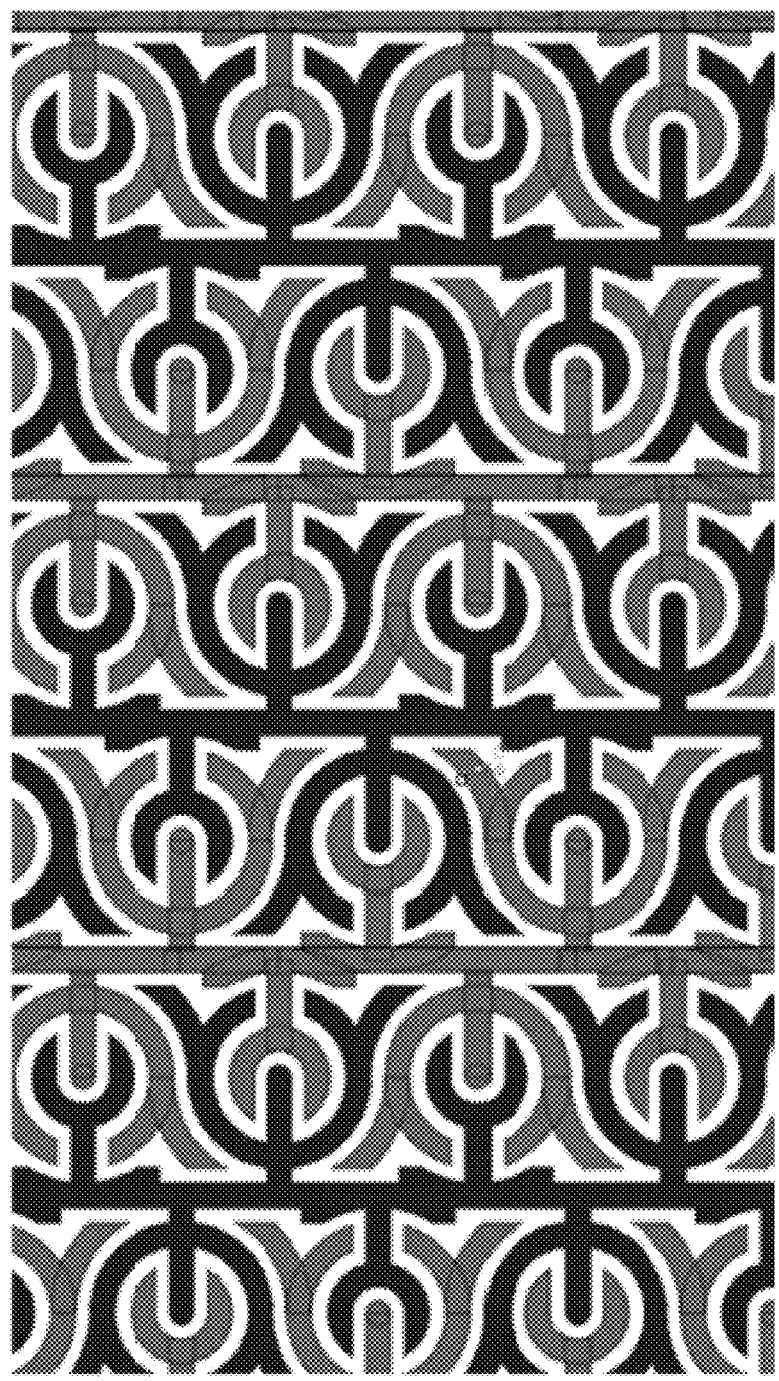
Figure 16D:
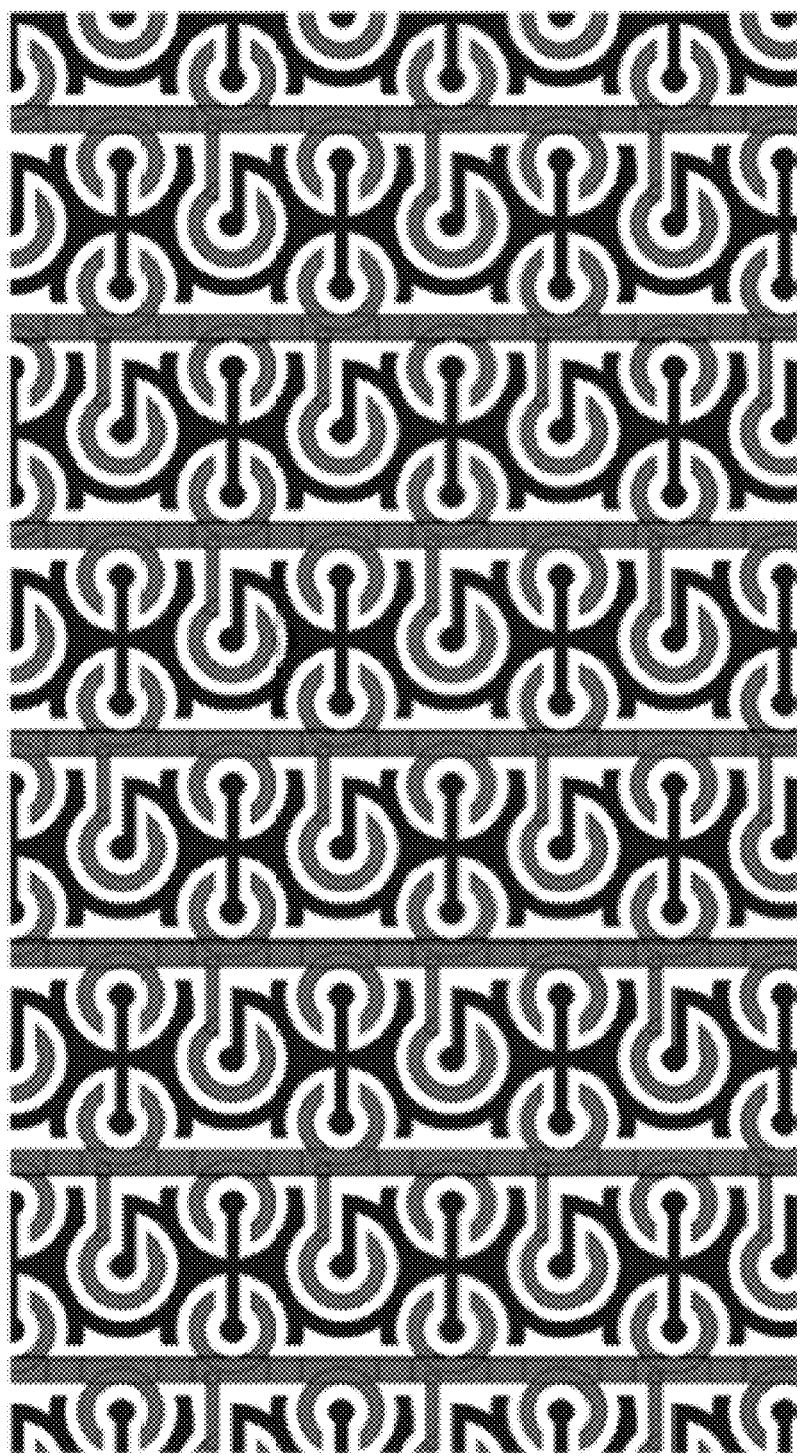
Figure 16E:
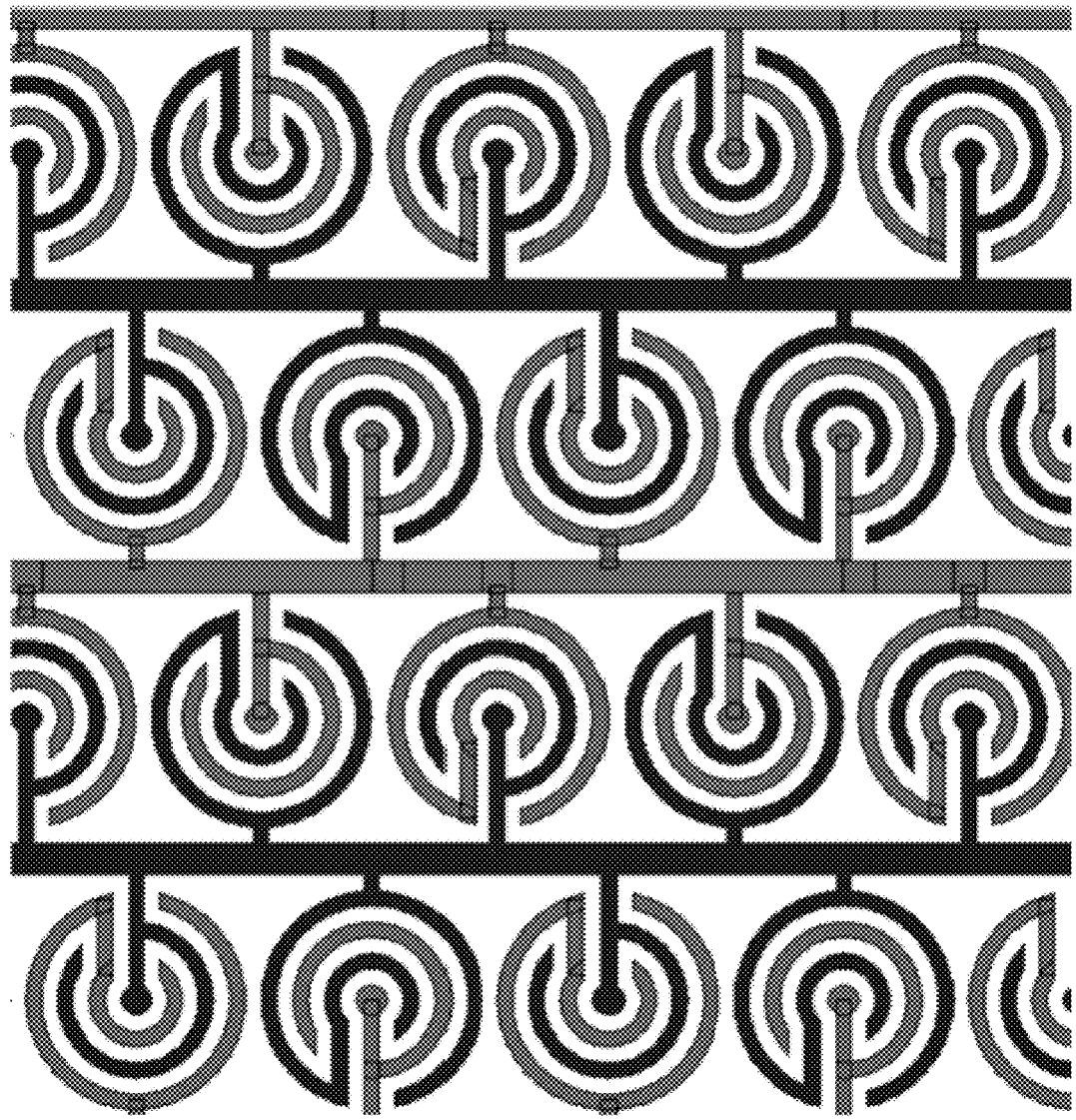
Figure 16F:
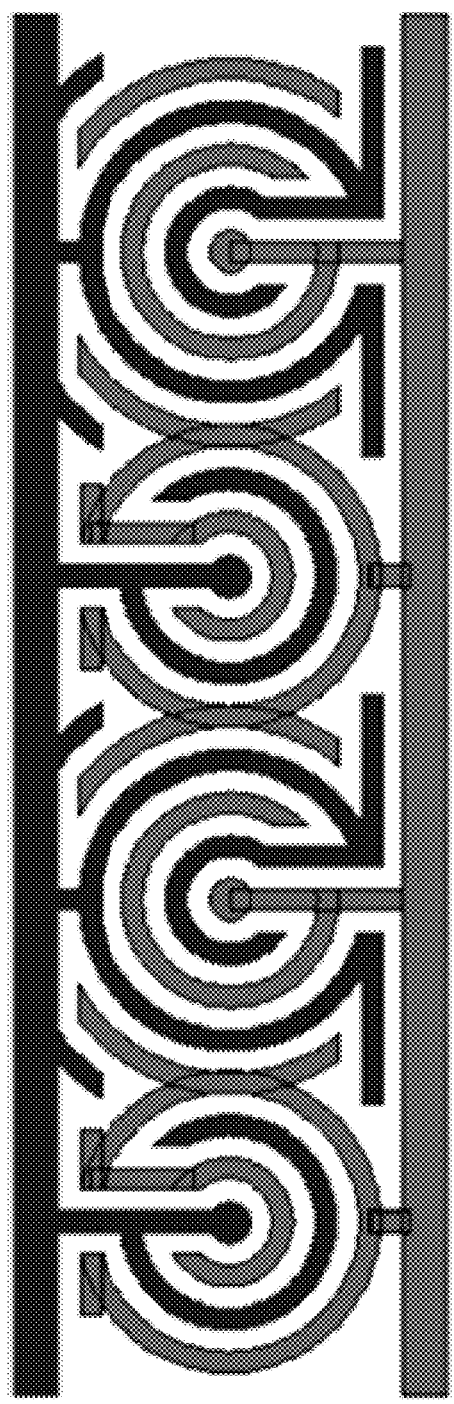
Figure 16G:
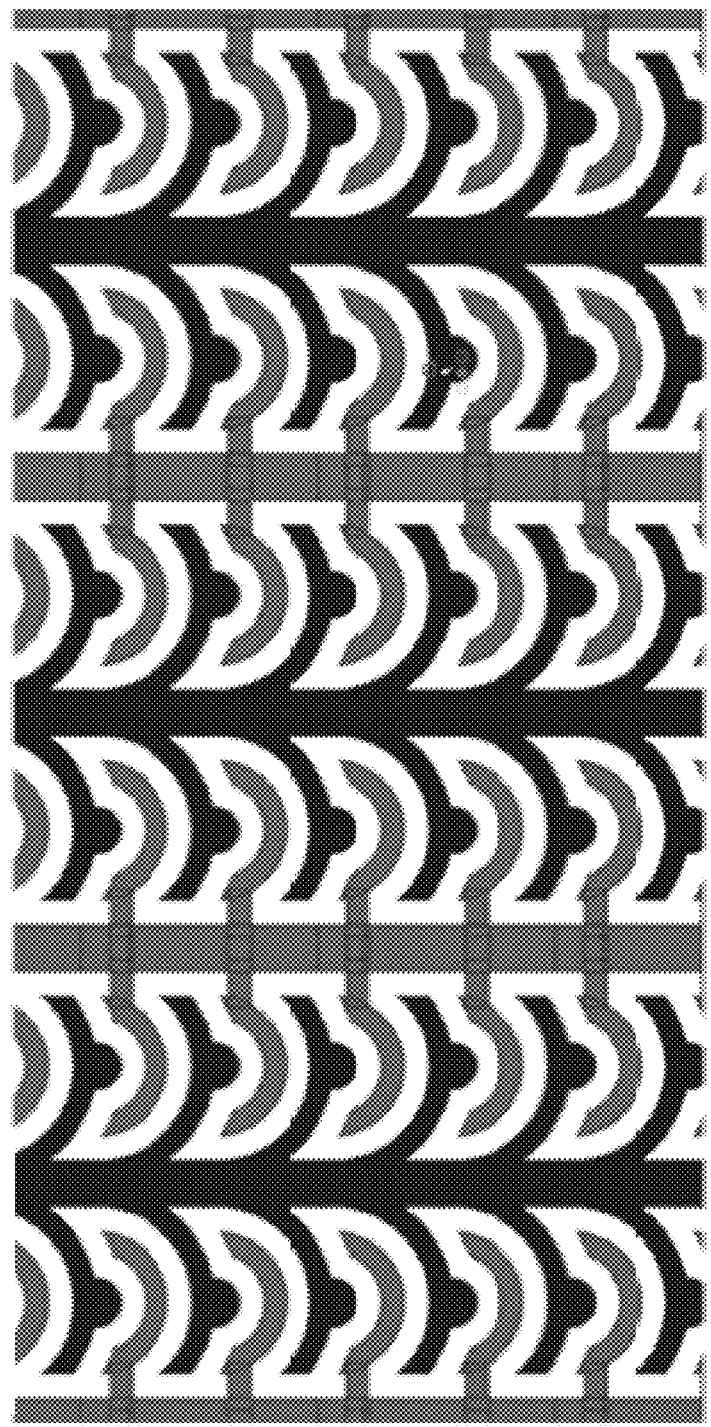
Figure 16H:
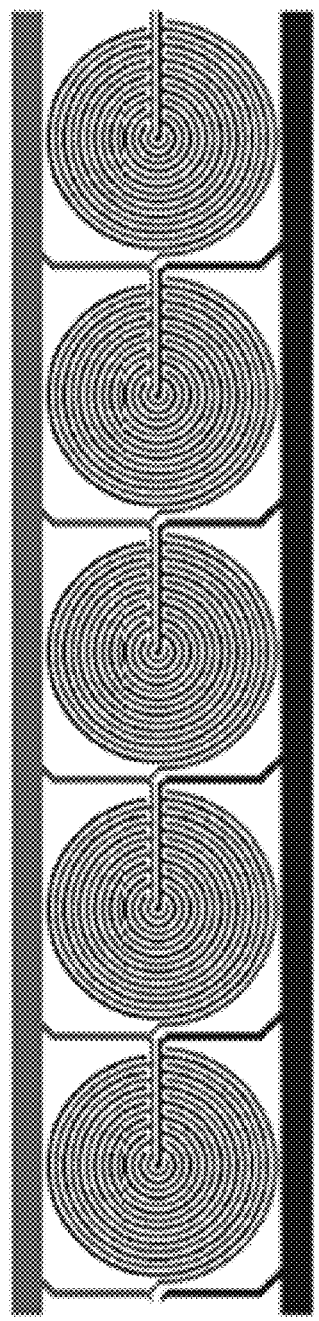

FIG. 16A shows the layout of a microfluidic device in accordance with some embodiments. FIGS. 16B-H illustrate different geometries of electrodes for high surface coverage to achieve high electric field gradients in accordance with some embodiments. In some embodiments, an electrode having one of the geometries shown in FIGS. 16A-H may cover the entire surface of a chamber (e.g., wall, top and/or bottom) of a fluidic device, examples of which are discussed above. The electrodes induce high field gradients, so that samples introduced into the chamber are exposed to high electric fields regardless of their position in the chamber. Such electrode design with a high surface coverage allows for control of over 99% of viral particles present in the sample and reduces false negatives.

As described herein, a further aspect in accordance with some embodiments involves the use of electroosmosis in addition to dielectrophoresis for transport. The frequencies at which electroosmosis are effective (e.g. tens of kHz) are widely separated from those useful in DEP, and therefore the two methods can be used simultaneously to provide a larger variety of separation regimes, and for a wider variety of objects to be separated.

In some embodiments, a high density gradient of electric field is induced by electrodes which are matched to viral size, so that viral particles are within 10-500 times the size of the electrode and/or electrode spacing.

Another aspect in accordance with some embodiments allows for use of a smartphone or other network-connected device for purposes of transmitting diagnostic information to a server adapted to store and analyze trends involving many diagnoses from multiple locations. This allows for tracking of the spread of disease, for example. A diagnostic device in accordance with some embodiments may be provided with communications functionality such as Bluetooth, Wi-Fi, NFC, or the like to communicate with network-connected devices such as a smartphone, PDA, laptop, router, desktop or other device. By sending information such as the number and type of viral particles detected, location, time, or other suitable information, the spread of particular viruses can be traced without requiring personal patient information. If patient information is sent, the diagnostic information gleaned by use of the device may be entered into patient profiles for access by subsequent physicians, researchers, and the like. Yet another aspect of some embodiments is directed to a function generator, frequency clock or data acquisition system connected to a smartphone that receives amplification and/or power from the smartphone.

(6) Example Protocols and Applications (a) Example Protocols

The following description provides examples of general protocols for practicing aspects of the technology described herein.

All viruses used in conducted experiments were suspended/diluted in a sterile phosphate buffered saline (PBS) pH 7.4 without calcium chloride and magnesium chloride diluted 1:1000 UltraPure Distilled Water. The conductivity of the PBS 1:1000 in DI water was in the range 19-23 µS/cm and was measured at room temperature (RT) using pH/mV/conductivity meter ACCUMET XL200. Aliquots of diluted PBS were stored at 4° C.

Human adenovirus 5 (Ad5) strain Adenoid 75 (ATCC-VR-5) were purchased from ATCC. To test Ad5 at certain concentration e.g. 1×105 infectious particles per milliliter (pfu/mL, plaque forming unit per milliliter), suspension of Ad5 was performed from freshly thawed in RT aliquots of virus stock in a PBS 1:1000 in DI water.

In some embodiments, to optically visualize Ad5 particles, the virus was stained with green fluorescent dye according to manufacture protocol. 1 mL of suspended Ad5 in PBS diluted 1:1000 in DI water 1 µL of SybrGreen I was added. The sample was mixed by vortexing for 5 seconds and then incubated 30 min in room temperature (RT) in darkness. After incubation time, the sample was mixed once again and was ready to process with static or flow Fluid-Screen Microfluidic System.

In some embodiments, to optically visualize Ad5 particles, the virus was stained with Alexa Fluor™ 594 or Alexa Fluor™ 610X NHS Ester (Succinimidyl Ester, ThermoFisher, USA). The virus concentration was verified by Bradford assay. The 450 µL of virus was mixed with sodium bicarbonate ($NaHCO_3$) for final concentration of 0.1 M. The 0.3-0.6% v/v Alexa Fluor™ 594 or Alexa Fluor™ 610X NHS Ester was added, and sample was incubated in darkness at RT for 90 min. After incubation time sample was mixed once again and was ready to process with static and flow Fluid-Screen Microfluidic System.

The high titer ($10^{10}$ pfu/mL) of pure rAAV full and empty capsids. To modulate electrical properties of rAAV mix of pure full and empty capsid (e.g. $10^7$ pfu of each) in PBS 1:1000 in DI water were incubated with 1-10% aqueous gadolinium acetate tetrahydrate (pH 7) (concentration must be determined experimentally) for 5 minutes to 1 hour (timing is critical and must be determined experimentally). After incubation time sample was mixed once again and was ready to process with static or flow Fluid-Screen Microfluidic System.

All tests ran on static microfluidic chip with electrodes, for example, as shown in FIG. 6, and was performed at RT. To evaluate Ad5 response to the electric field virus sample was stained with SybrGreen I and 3 µL of sample was loaded to the chip. When capillary flow stabilized, electric field 50 V peak to peak (Vpp) was applied at 10 kHz frequency and sequentially increased up to 1 MHz with intervals of 10 kHz.

Then frequency was increased from 5 MHz to 50 MHz with intervals of 5 MHz. Finally, frequency was increased up to 90 MHz accompanied with maximal voltage. Captured virus particles on spiral of static chip were visualized using a fluorescent microscope (Olympus, USA).

The inventors have recognized that the frequency and/or amplitude of the electric field produced by the electrodes may be tuned to induce a response in protein structures of viral particles. Furthermore, the operation of the microfluidic chamber having electrodes with an applied electric field may involve tuning the frequency of the applied electric field such that the response of protein structures forming a full capsid is differential compared to the response of protein structures forming an empty capsid, thereby allowing for rapid purification/separation of empty capsids from fully packaged genomes.

Furthermore, the operation of the microfluidic system with an applied electric field of a certain frequency may be such that the response of chemically modified protein structures that form a full capsid is differential compared to the response of chemically modified protein structures that form an empty capsid (e.g., by labeling empty capsids with gadolinium triacetate, as described herein).

The inventors have recognized that the use of the microfluidic system may involve the use of multiple microfluidic chambers to perform rapid detection, separation, quantification and/or purification of a fluid sample containing viral particles. For example, one or more microfluidic chambers of a microfluidic system may be used to purify 1 mL or more of substance. In some embodiments, one or more microfluidic chambers may be used to purify 100 mL or more of substance at a time.

The purification processes described herein may be performed rapidly, despite also being performed on a large scale. For example, in some embodiments, the purification process may use one or more microfluidic chambers of the microfluidic system to purify 100 mL of fluid in less than 8 hours. In some embodiments, the purification process may use one or more microfluidic chambers of the microfluidic system to purify 100 mL of fluid in less than 3 hours.

The inventors have recognized that the apparatus and methods described herein provide for a high separation efficiency of viral particles from a sample, including for example, separating fully packaged capsids from empty and/or partially filled capsids. In some embodiments, separation efficiency of empty/partially filled capsid to full capsid according to the separation and purification methods described herein may be at least 95%. Furthermore, high separation efficiencies, including 95% separation efficiencies, may be realized for both small and large scale separation. For example, separation efficiencies of 95% may be possible for purification methods with fluid samples of 1 mL or more, as well as fluid samples of 100 mL or more.

(b) Example Applications

The inventors have recognized that the techniques described herein for viral detection, separation, purification and/or quantification may be useful in a number of contexts, examples are which are further described as follows.

(i) Drug Manufacturing

One application of the techniques described herein is drug manufacturing, where the end product of the manufacturing process is the drug itself which contains viral particles. In some instances, it is required that a drug contain a particular concentration of full capsid viral particles. This may mean that the drug contains only full capsid viral particles and no empty and/or partially filled capsids, or that the percentage of empty and/or partially filled capsids or ratio of empty and/or partially filled capsids to full capsids is kept at a certain amount or target range.

The inventors have recognized that the techniques described herein for purifying a sample by removing some or all components other than viral particles (e.g., empty and/or partially filled capsids) may be used to assist the drug manufacturing process. For example, a microfluidic device as described herein may be coupled to a bioreactor containing samples for drug manufacturing. In some embodiments, the microfluidic device is not in-line with a bioreactor but is configured such that manual transfer of samples from the bioreactor to the microfluidic device may be performed. Samples from the bioreactor may be processed using the microfluidic device to separate and partially and fully remove empty and/or partially filled capsids from the sample. The purified sample may then be used to manufacture a drug containing a requisite amount of viral particles.

(ii) Drug Characterization

Another application of the techniques described herein is in drug characterization. For example, characterizing a sample may include analyzing a sample of the drug to determine an amount of full capsid viral particles in the sample and/or an amount of other components (such as empty and/or partially filled capsids) in the sample. Such quantification may be performed using a microfluidic device according to the techniques described herein.

For example, DEP and/or EO forces generated by an electrode of a microfluidic device may be used to separate full capsid viral particles of a sample from other components (e.g., empty and/or partially filled capsids). The separated components may be quantified to determine a ratio of viral particles to other components of the sample (e.g., a ratio of full capsids to empty and/or partially filled capsids).

In some embodiments, an amount of viral particles may be determined to obtain the ratio of viral particles to other components. In some embodiments, a ratio of viral particles to other components may be determined without determining an amount of individual particles in a sample. Instead, groupings of accumulated viral particles may be compared to groupings of accumulated non-viral particles.

In some embodiments, the determined ratio may be used to optimize the drug manufacturing process. For example, if the determined ratio is indicated to be too low (e.g., having too few viral particles) or too high (e.g., having too many viral particles), the manufacturing process may be adjusted in order to increase or decrease the ratio of viral particles to other components of the sample as desired. In some embodiments, the determined ratio may be used to satisfy reporting requirements, such as those required by the Food and Drug Administration.

(iii) Contamination Detection

A further application of the techniques described herein is in detecting contamination in a sample, such as in a pharmaceutical manufacturing process, in some embodiments. For example, the techniques described herein may be applied to facilitate detection of viral particles in a sample. As described herein, existing methods for detecting viral contamination are length, often taking up to 60 days to determine whether a sample is contaminated. In addition, visualization of viral particles in a sample is difficult given the small size of viruses. Processing a sample with a microfluidic device according to the techniques described herein, however, can aggregate viral particles together to increase the ease of detecting such particles. In addition, as described herein, the viral particles may be labeled to further enhance visualization.

(iv) Diagnostics

A further application of the techniques described herein is in diagnostics. In particular, the inventors have appreciated that diagnostic tests for viral infections are limited at least due to the difficulty in detecting viruses of small sizes and in detecting viruses in the presence of large quantities of other components in the background of a sample. The inventors have recognized that the techniques described herein may be used to (1) reduce the amount of background components by separating other components from viral particles and (2) immobilizing and aggregating the viral particles to a region on the surface of an electrode to reduce the difficulty in detecting individual viral particles. According to the techniques described herein, viral infection detection may be performed in shorter time frames, reducing the length of time an individual may need to be quarantined.

(v) Vaccine Development

In some embodiments, the techniques described herein may be applied to vaccine development. For example, vaccines may require a particular concentration of viral particles. Attenuation of viral particles trapped on the surface of a microfluidic device may be performed, using, for example, an applied electric field, heat, chemicals, radiation, ultraviolet light, and/or any other suitable technique. The microfluidic techniques described herein may be used to quantify and/or achieve a particular concentration of viral particles in a sample used for vaccine development. Further, the inventors have recognized that, in contrast to conventional techniques, processing of a sample with a microfluidic device to detect, separate, purify, and/or quantify viral particles in the sample does not affect an infectivity of the viral particles. As such the samples may be used in manufactured products such as vaccines or drugs containing viral particles even after processing with a microfluidic device.

(7) Example Computing Devices

Figure 17:
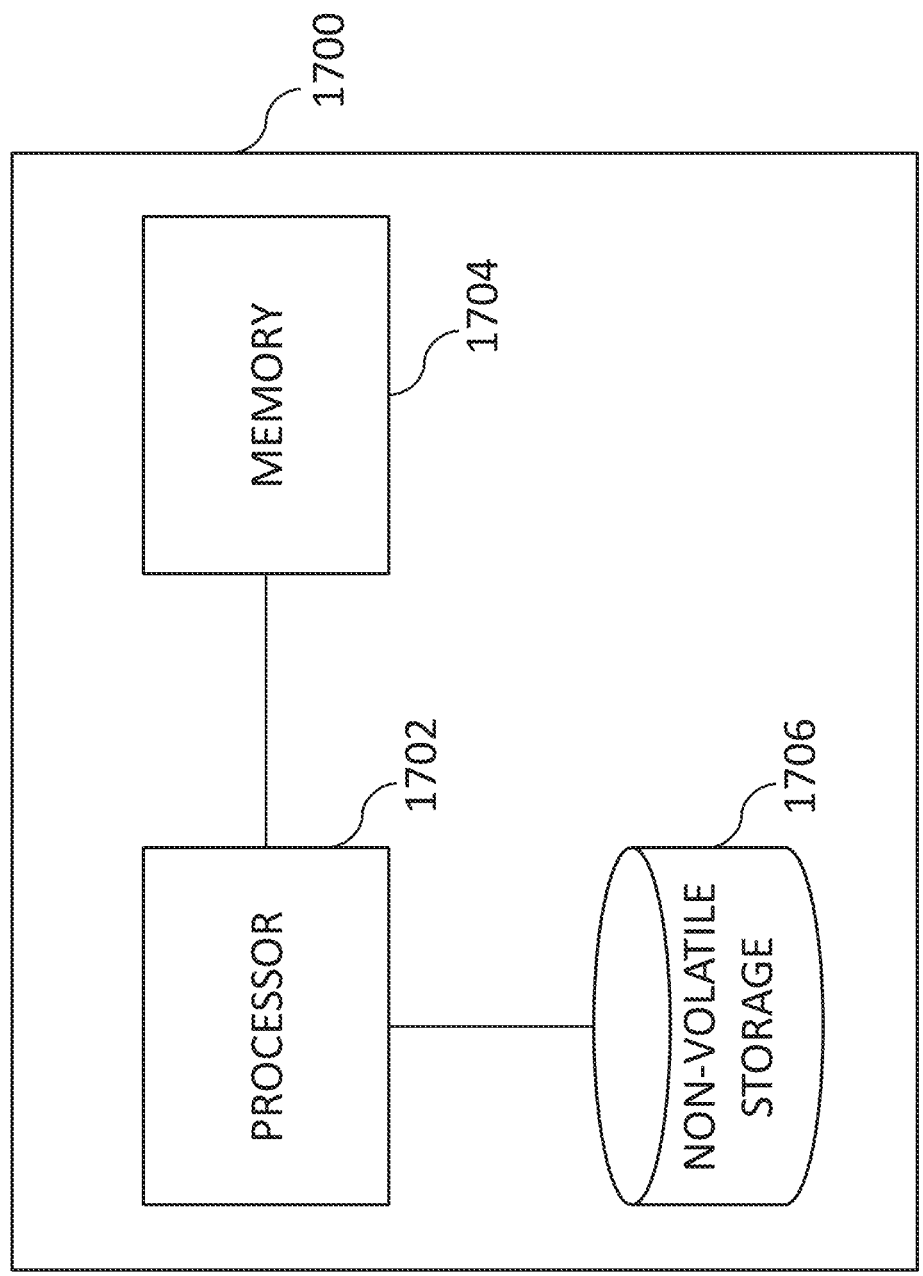
FIG. 17 shows a block diagram of an example computer system that may be used to implement embodiments of the technology described herein.

FIG. 17 shows a block diagram of an example computer system 1700 that may be used to implement embodiments of the technology described herein. The computing device 1700 may include one or more computer hardware processors 1702 and non-transitory computer-readable storage media (e.g., memory 1704 and one or more non-volatile storage devices 1706). The processor(s) 1702 may control writing data to and reading data from (1) the memory 1704; and (2) the non-volatile storage device(s) 1706. To perform any of the functionality described herein, the processor(s) 1702 may execute one or more processor-executable instructions stored in one or more non-transitory computer-readable storage media (e.g., the memory 1704), which may serve as non-transitory computer-readable storage media storing processor-executable instructions for execution by the processor(s) 1702.

(8) Alternatives and Scope

Having thus described several aspects and embodiments of the technology set forth in the disclosure, it is to be appreciated that various alterations, modifications, and improvements will readily occur to those skilled in the art. For example, while aspects of the present technology relate to an apparatus and methods for detection, separation, purification, and/or quantification of viral particles as described herein, the inventors have recognized that such apparatus and methods are broadly applicable to other pathogens of interest, e.g. bacterial particles, and aspects of the technology are not limited in this respect.

Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated, that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "substantially", "approximately", and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

User of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method for separating components of a sample, the components comprising full capsid viral particles and empty and/or partially filled capsids, the method comprising:

labeling the sample with a chemical agent, wherein the labeling modifies a response of the empty and/or partially filled capsids to at least one dielectrophoretic force acting on the sample relative to a response of the full capsid viral particles to the at least one dielectrophoretic force acting on the sample;

directing the sample through at least one channel of a microfluidic device having at least one electrode arranged therein;

separating the full capsid viral particles from the empty and/or partially filled capsids at least in part by generating, using the at least one electrode, the at least one dielectrophoretic force that acts on the sample, wherein the empty and/or partially filled capsids respond differently to the at least one dielectrophoretic force than the full capsid viral particles at least in part due to the labeling; and differentiating between the empty and/or partially filled capsids and the full capsid viral particles based on responses of the components of the sample to the at least one dielectrophoretic force.

2. The method of claim 1, wherein the labeling increases a difference between a dielectric function and/or a complex permittivity of each empty and/or partially filled capsid and a dielectric function and/or a complex permittivity of each full capsid viral particle.

3. The method of claim 1, wherein the chemical agent comprises gadolinium triacetate.

4. The method of claim 1, wherein the labeling increases a difference between a mass of each empty and/or partially filed capsid and a mass of each full capsid viral particle.

5. The method of claim 1, further comprising determining a ratio of full capsid viral particles to empty and/or partially filled capsids.

6. The method of claim 1, further comprising separating the full capsid viral particles from the empty and/or partially filled capsids by condensing the full capsid viral particles into a region.

7. The method of claim 1, further comprising flushing the empty and/or partially filled capsids from a region of the microfluidic device containing the at least one electrode.

8. The method of claim 1, wherein the at least one electrode comprises at least one circular-shaped and/or partially-center-symmetric electrode.

9. The method of claim 1, wherein an infectivity of the full capsid viral particles is unaffected by the labeling, directing, generating, and differentiating.

10. The method of claim 1, wherein each of the full capsid viral particles and the empty and/or partially filled capsids have a diameter of 400 nm or less.

11. A system configured to separate components of a sample, the components comprising full capsid viral particles and empty and/or partially filled capsids, the system comprising:

a microfluidic device comprising at least one channel having at least one electrode arranged therein, wherein the at least one channel is configured to receive the sample; and a controller configured to:
direct the sample through the at least one channel of the microfluidic device, the sample being labeled with a chemical agent that modifies a response of the empty and/or partially filled capsids to at least one dielectrophoretic force acting on the sample relative to a response of the full capsid viral particles to the at least one dielectrophoretic force acting on the sample;

separate the full capsid viral particles from the empty and/or partially filled capsids at least in part by generating, using the at least one electrode, the at least one dielectrophoretic force that acts on the sample, wherein the empty and/or partially filed capsids respond differently to the at least one dielectrophoretic force than the full capsid viral particles at least in part due to the labeling; and differentiate between the empty and/or partially filled capsids and the full capsid viral particles based on responses of the components of the sample to the at least one dielectrophoretic force.

12. The system of claim 11, wherein the labeling increases a difference between a dielectric function and/or a complex permittivity of each empty and/or partially filled capsid and a dielectric function and/or a complex permittivity of each full capsid viral particle.

13. The system of claim 11, wherein the chemical agent comprises gadolinium triacetate.

14. The system of claim 11, wherein the labeling increases a difference between a mass of each empty and/or partially filed capsid and a mass of each full capsid viral particle.

15. The system of claim 11, wherein the controller is further configured to determine a ratio of full capsid viral particles to empty and/or partially filled capsids.

16. The system of claim 11, wherein the controller is further configured to separate the full capsid viral particles from the empty and/or partially filled capsids by condensing the full capsid viral particles into a region.

17. The system of claim 11, wherein the controller is further configured to flush the empty and/or partially filled capsids from a region of the microfluidic device containing the at least one electrode.

18. The system of claim 11, wherein the at least one electrode comprises at least one circular-shaped and/or partially-center-symmetric electrode.

19. The system of claim 11, wherein an infectivity of the full capsid viral particles is unaffected by the directing, generating, and differentiating.

20. The system of claim 11, wherein each of the full capsid viral particles and the empty and/or partially filled capsids have a diameter of 400 nm or less.

* * * * *